US010850085B2

(12) United States Patent
Tekeste

(10) Patent No.: US 10,850,085 B2
(45) Date of Patent: Dec. 1, 2020

(54) METHODS AND APPARATUS FOR DISINFECTING AND REFLUX PREVENTION FLUSH SYRINGE ASSEMBLY

(71) Applicant: Becton, Dickinson and Company, Franklin Lanes, NJ (US)

(72) Inventor: Girum Yemane Tekeste, Hackensack, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 204 days.

(21) Appl. No.: 16/018,707

(22) Filed: Jun. 26, 2018

(65) Prior Publication Data

US 2018/0304064 A1 Oct. 25, 2018

Related U.S. Application Data

(60) Continuation of application No. 14/973,863, filed on Dec. 18, 2015, now Pat. No. 10,022,530, which is a
(Continued)

(51) Int. Cl.
*A61M 39/16* (2006.01)
*A61M 39/02* (2006.01)
(Continued)

(52) U.S. Cl.
CPC ...... *A61M 39/0247* (2013.01); *A61M 5/3134* (2013.01); *A61M 5/3146* (2013.01); *A61M 5/31511* (2013.01); *A61M 5/31515* (2013.01); *A61M 5/345* (2013.01); *A61M 39/16* (2013.01); *A61M 2005/312* (2013.01); *A61M 2005/3103* (2013.01); *A61M 2005/3104* (2013.01); *A61M 2005/31523* (2013.01);
(Continued)

(58) Field of Classification Search
CPC .. A61M 2005/3103; A61M 2005/3104; A61M 39/16; A61M 5/3134
USPC .......................................................... 604/265
See application file for complete search history.

(56) References Cited

U.S. PATENT DOCUMENTS 5,647,849 A 7/1997 Kalin
9,943,676 B2 * 4/2018 Tekeste ............... A61M 5/3134
(Continued)

FOREIGN PATENT DOCUMENTS

GB 2114006 A 8/1983
JP 2000505658 A 5/2000
(Continued)

OTHER PUBLICATIONS

Extended European Search Report in EP 17163881.0 dated Aug. 1, 2017, 7 pages.
(Continued)

*Primary Examiner* — Deanna K Hall
(74) *Attorney, Agent, or Firm* — Servilla Whitney LLC

(57) ABSTRACT

Embodiments of the invention are directed to flush syringe assemblies comprising an integrated contamination-prevention device integrated with device connector flushing positioned so that the practitioner cannot forget to apply disinfectant. The flush syringe assemblies comprise a barrel with an elongate plunger rod disposed therein and a cap comprising a passageway. The plunger rod includes a stopper of which at least a portion can be embedded in the passageway of the cap to form a plug in the cap.

18 Claims, 23 Drawing Sheets

Related U.S. Application Data division of application No. 13/689,095, filed on Nov. 29, 2012, now Pat. No. 9,233,208.

(51) Int. Cl.
  *A61M 5/31*    (2006.01)
  *A61M 5/315*   (2006.01)
  *A61M 5/34*    (2006.01)
  *A61M 39/10*   (2006.01)
  *A61M 39/00*   (2006.01)

(52) U.S. Cl.
  CPC ............ *A61M 2039/0018* (2013.01); *A61M 2039/0205* (2013.01); *A61M 2039/0258* (2013.01); *A61M 2039/0285* (2013.01); *A61M 2039/1077* (2013.01); *A61M 2202/0468* (2013.01); *A61M 2202/0484* (2013.01)

(56) References Cited

U.S. PATENT DOCUMENTS

| | | |
|---|---|---|
| 2004/0082911 A1 | 4/2004 | Tiu et al. |
| 2005/0154353 A1 | 7/2005 | Alheidt |
| 2008/0033371 A1 | 2/2008 | Updegraff et al. |
| 2008/0097242 A1 | 4/2008 | Cai |
| 2008/0300551 A1 | 12/2008 | Schiller et al. |
| 2009/0062766 A1 | 3/2009 | Howlett et al. |
| 2009/0247958 A1* | 10/2009 | Carlyon .............. A61M 5/3134 604/222 |
| 2009/0247961 A1 | 10/2009 | Carlyon |
| 2011/0034882 A1 | 2/2011 | Quinn et al. |

FOREIGN PATENT DOCUMENTS

| | | |
|---|---|---|
| JP | 2012029724 A | 2/2012 |
| JP | 2012075901 A | 4/2012 |
| WO | 2011028722 A2 | 3/2011 |
| WO | 2011110888 A1 | 9/2011 |
| WO | 2012135943 A1 | 10/2012 |

OTHER PUBLICATIONS

Non-Final Office Action in U.S. Appl. No. 14/973,863, dated Oct. 31, 2017, 12 pgs.
Non-Final Office Action in U.S. Appl. No. 14/973,872 dated Oct. 19, 2017, 7 pages.
PCT International Search Report and Written Opinion in PCT/US2013/071892, dated Feb. 24, 2014, 11 pages.
Vital Signs: Central Line—Associated Blood Stream Infections—United States, 2001, 2008, and 2009, MMWR Morb. Mortal Wkly. Rep., 2011, pp. 60:243-248.

* cited by examiner

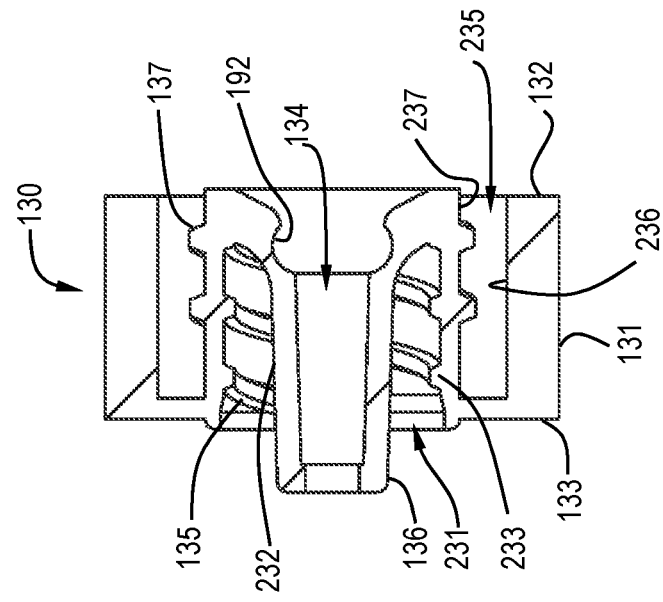
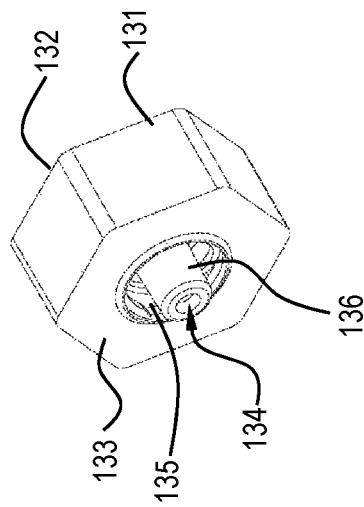
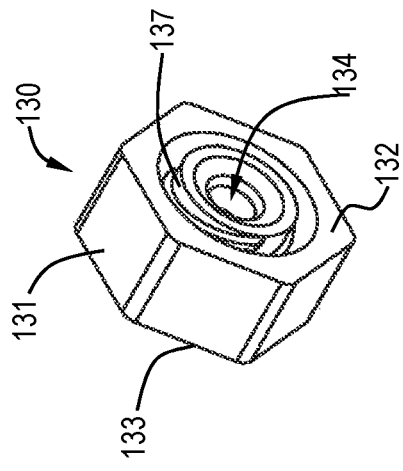

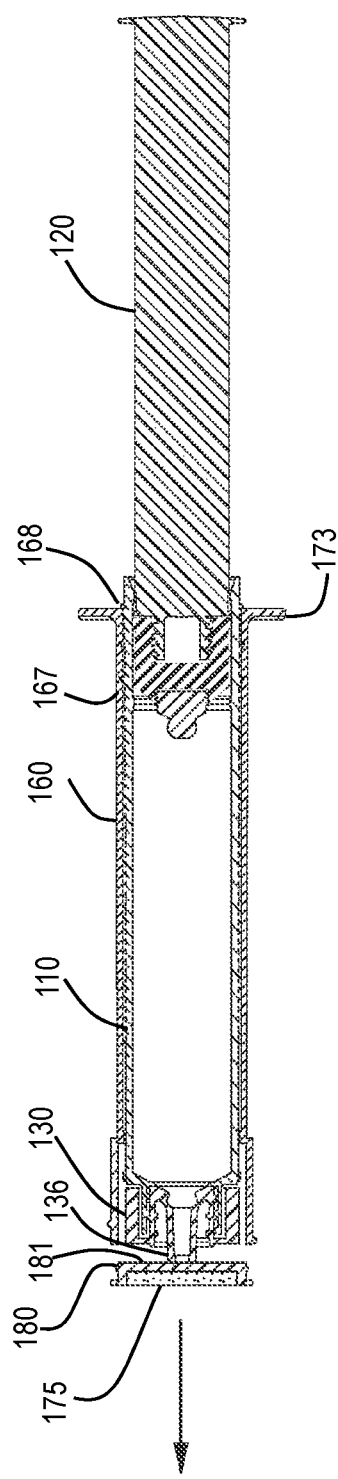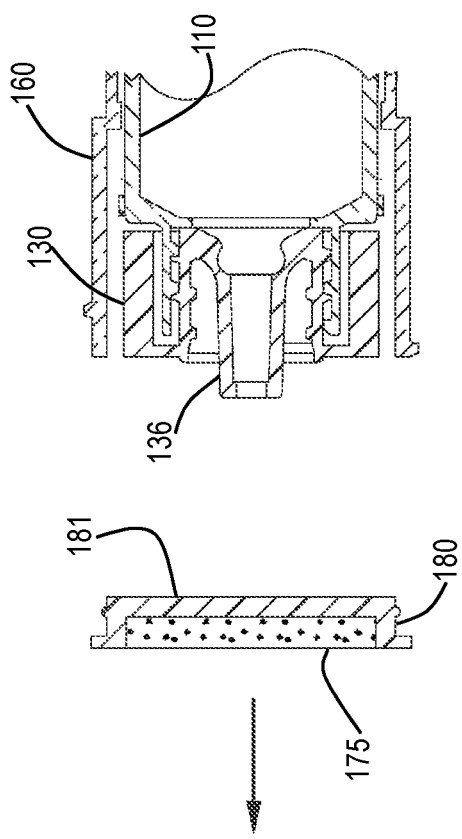
FIG. 18
FIG. 19

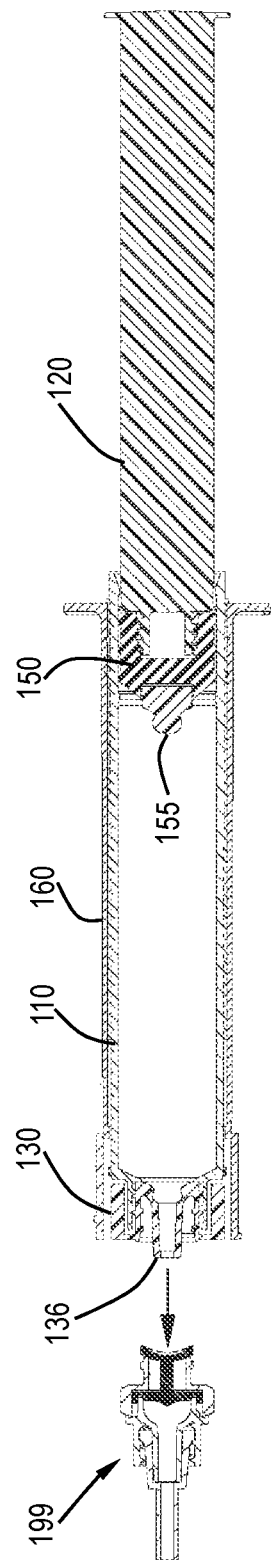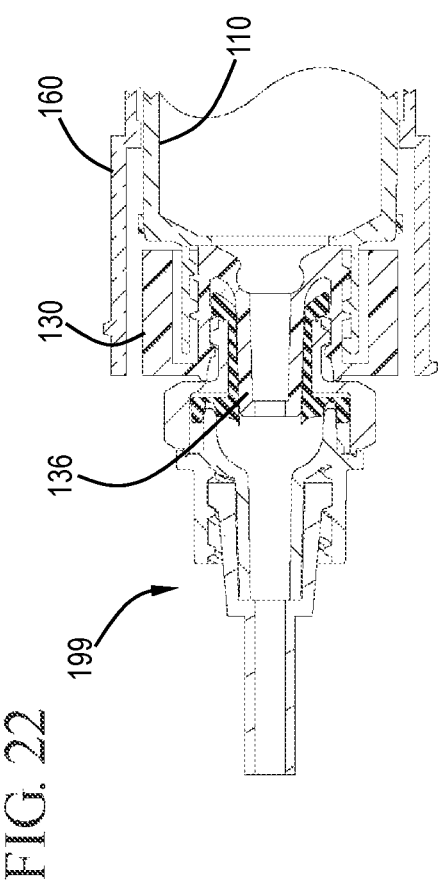
FIG. 21
FIG. 22

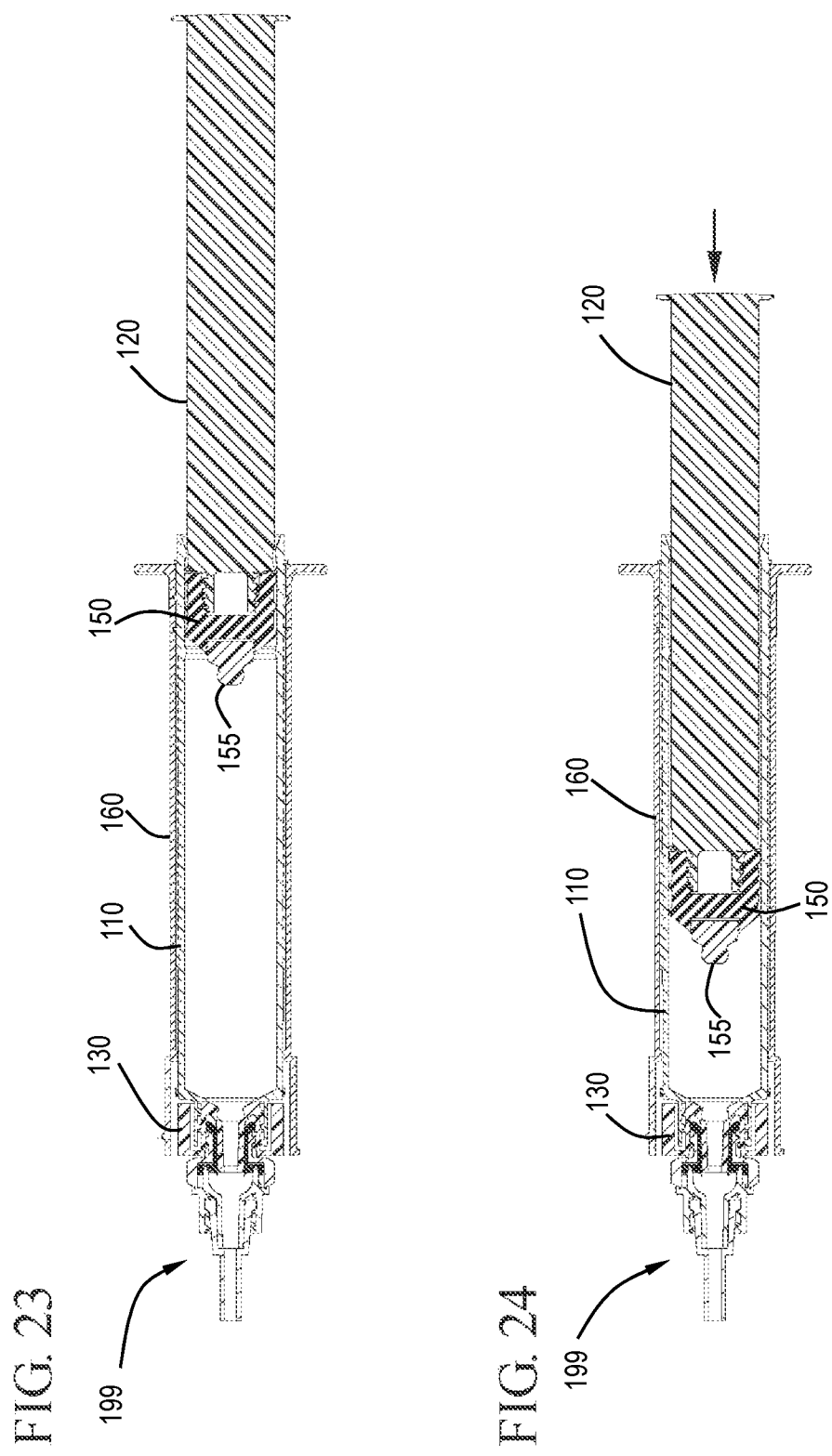

METHODS AND APPARATUS FOR DISINFECTING AND REFLUX PREVENTION FLUSH SYRINGE ASSEMBLY

CROSS-REFERENCE TO RELATED APPLICATIONS

This application is continuation of U.S. patent application Ser. No. 14/973,863, filed Dec. 18, 2015, which is a divisional of U.S. patent application Ser. No. 13/689,095, filed Nov. 29, 2012, the entire disclosures of which are hereby incorporated by reference herein.

FIELD

Embodiments of the invention generally relate to apparatus and methods to prevent blood reflux in vascular access devices (VAD). More specifically, embodiments of the invention are directed to technology to reduce the risk for bloodstream infections (CRBSI) and intravenous (IV) line patency maintenance including one or more of IV connectors cleaning, reflux prevention, connector capping technology, syringe assemblies and particularly to syringe assemblies for use in flush procedures, for vascular access devices (VADs) such as peripheral catheters and central venous catheters.

BACKGROUND

VADs are commonly used therapeutic devices yet accounted for 18,000 blood stream infections in American ICUs in 2009, according to the CDC, which also reports a mortality rate of 12-25%. *MMWR Morb. Mortal Wkly. Rep.* 2011; 60:243-248. In the same article, the CDC attributes additional blood stream infections and deaths to VAD use in regular hospital rooms and out-patient care.

If not properly maintained the VADs, which include peripheral catheters and central venous catheters, can become sealed with blood clots or spread infection. To ensure VADs are used properly and do not become sealed or infected, protocols have been developed. These protocols include sterilizing the VAD and the flushing the catheter with a flush solution. VAD protocols usually recommend flush procedures be performed after catheter placement, before fluid infusion, and before and after drug administration, blood sampling, transfusions and parenteral nutrition. The goal of these flush procedures is to confirm catheter patency, avoid drug incompatibilities, ensure the complete drug dose administration, prevent thrombus formation and minimize the risk of blood stream infections. Before each flush procedure is performed, the VAD should be sterilized. A recent study reported that 30% of the time, there is no effort to sterilize the VAD prior to flushing and when an attempt to sterilize the VAD it often did not fully meet aseptic practices.

Catheters are flushed using syringe assemblies filled with various fluids. In some cases, different fluids are injected sequentially in accordance with the protocol. For example, a saline solution followed by an anticoagulant such as heparin. The size of the syringe used to flush I.V. lines varies by various factors including the size and length of the catheter. Typically syringes of 1 ml, 3 ml, 5 ml and 10 ml volume are used.

It is important in the flush procedure not to draw blood back into the catheter where it can clot and seal the catheter, commonly referred to as "reflux". In order to prevent blood reflux into the catheter the user is encouraged to maintain a positive pressure in the line during the flush procedure. This may involve clamping the IV line and Withdrawing the syringe and cannula from the I.V. port while still applying pressure to the syringe plunger rod during the flush procedure. When using a syringe with an elastomeric stopper, the stopper is often compressed when it contacts the distal end of the syringe barrel at the completion of the flush procedure. When a user relieves the pressure to the plunger after the flush procedure is completed, the stopper will expand back to its normal size thereby withdrawing liquid from the catheter into the syringe barrel. This is undesirable, since it can cause blood to enter the catheter at the catheter distal end (reflux) where it will remain stationary until the next time the VAD is used.

IV lines are now being flushed by a wide variety of health care workers, not just those who in the past were dedicated to catheter maintenance. In the case of out-patient care, the patients themselves may even flush their own catheters. These less experienced persons might prematurely release the compressive force on the stopper or use excessive force which would deform the stopper, either which may draw blood into the catheter and cause reflux of blood. Consequently, there is a need for flush syringe assemblies which promote sterilizing the VAD and help reduce or eliminate reflux of blood during the flushing procedure even if flush protocols are not precisely followed.

SUMMARY

One or more embodiments of the invention are directed to flush syringe assemblies comprising a barrel, an elongate plunger rod, a cap, a sleeve and a disinfecting system. The barrel includes a side wall having an inside surface defining a chamber for retaining fluid, an outside surface, an open proximal end, a distal end including a distal wall having a passageway therethrough in fluid communication with the chamber. The elongate plunger rod is disposed within the barrel. The plunger rod comprises a distal end including a stopper slidably positioned in fluid-tight contact with the inside surface of the barrel for driving fluid out of the chamber by movement of the stopper relative to the barrel. The stopper comprises a stopper body and a detachable stopper tip. The cap comprises an outer wall surrounding a Luer connection. The cap comprises a passageway for fluid communication therethrough, wherein the passageway is undercut to receive and retain the stopper tip when the plunger rod is fully depressed. The cap further comprises a distal end for releasably attaching the cap to a vascular access device (VAD) and a proximal end for releasably attaching the cap to the barrel. The sleeve is external to the barrel and has a distal end and a proximal end, and an inside surface and an outside surface. The sleeve slides from distal to proximal positions in relationship to the barrel. The disinfecting system comprises a disinfectant contained in a hub, wherein the disinfecting system is released upon proximal motion of the sleeve.

In some embodiments, the cap is threaded to engage complementary threads on the VAD. In one or more embodiments, the cap engages the VAD with an interference fit. In certain embodiments, the passageway of the cap is coated with an antimicrobial agent.

In some embodiments, the undercut of the passageway of the cap creates a tight interference fit sufficient for retaining the stopper tip within the cap upon movement of the plunger rod away from the cap after emptying the fluid from the syringe.

In one or more embodiments, the stopper tip has threads which engage with complementary threads on the stopper body. In some embodiments, the stopper tip is secured to the stopper body using an interference fit. In detailed embodiments, the stopper body is made of material selected from the list consisting of thermoplastic elastomers, natural rubber, synthetic rubber, thermoplastic materials and combinations thereof. In certain embodiments, the stopper tip is made of material selected from the list consisting of thermoplastic elastomers, natural rubber, synthetic rubber, thermoplastic materials and combinations thereof.

In one or more embodiments, the outside surface of the barrel further comprises two annular positioning ridges, a distal annular positioning ridge and a proximal annular positioning ridge. In some embodiments, the inside surface of the sleeve further comprises at least one annular positioning groove for controlling the position of the sleeve relative to the barrel by engaging with the annular positioning ridges on the outside surface of the barrel. In detailed embodiments, the outside surface of the barrel comprises one or more ridges that extend along a length of the barrel and engage with the corresponding groove on the inside surface of the sleeve.

In some embodiments, the plunger is of sufficient length relative to the sleeve and the barrel that when plunger is fully depressed after all flushing solution has been expelled from the syringe, the sleeve retracts to expose the cap.

In some embodiments, the sleeve further comprises one or more cutouts to provide visibility to the flush solution of the barrel. In one or more embodiments, the distal end of the sleeve is threaded to engage complementary threads on the disinfecting system. In specific embodiments, the distal end of the sleeve is attached to the disinfecting system using an interference fit.

In some embodiments, the disinfecting system further comprises a removable cover to protect the disinfecting system prior to use and a disinfectant carrier. In one or more embodiments, the disinfectant is made of material selected from the group consisting of: alcohol, an antiseptic gel, and combinations thereof.

Additional embodiments of the invention are directed to methods of flushing a VAD. A flush syringe assembly, as described herein, is provided. The protective cover is removed using one hand from the distal end of the flush syringe assembly thereby exposing a disinfectant contained at the distal end of the syringe assembly. The disinfectant is applied to the VAD connector using one hand. The same hand ejects the disinfecting system. The flush syringe assembly is coupled to the VAD. Using one hand, the flush syringe assembly is held and the plunger is depressed to flush the VAD with a flush solution that is contained in the chamber. Using the same hand to continue to depress the plunger after the barrel is empty to embed the stopper tip into the VAD and retract the sleeve to expose the cap. The cap including the embedded stopper tip is separated from the flush syringe assembly.

In some embodiments, the method further comprises removing the cap including the embedded stopper tip and repeating the steps through separating the cap including the stopper tip from the flush syringe assembly.

Further embodiments of the invention are directed to flush syringe assemblies comprising a barrel, a cap, a releasable disinfecting system, an elongate plunger rod, a sleeve and a quantity of flush solution. The barrel includes a side wall having an inside surface defining a chamber for retaining fluid, an outside surface, an open proximal end, a distal end including a distal wall with a tip extending distally therefrom having a passageway therethrough in fluid communication with the chamber. The barrel further comprises an outside surface containing one or more annular positioning discontinuity. The cap comprises a distal end and a proximal end defining a length, an irregularly shaped outer wall, a profiled center passageway providing fluid communication from the chamber to a patient's vascular access device (VAD). The cap further comprises a distal end annular channel that releasably attaches the cap to the VAD, and a proximal end annular channel that releasably attaches the cap to the barrel. The releasable disinfecting system comprises a disinfectant. The elongate plunger rod is disposed within the barrel and comprises a distal portion and a proximal portion. The plunger rod further comprises a distal end including a stopper slidably positioned in fluid-tight contact with the barrel inside surface for expelling fluid from the chamber by movement of the stopper relative to the barrel. The stopper has a distal face and a proximal end. The distal face of the stopper further comprises a profiled stopper tip that is detachable from the stopper and seatable in the cap when the plunger rod is fully depressed. The sleeve is external to the barrel and has an inside surface and an outside surface, an open proximal end containing at least one flange, and an open distal end defining a recess with an irregular inner surface to contain and prevent rotation of the cap relative to the sleeve. The distal end is further connected to the releasable disinfecting system. The sleeve further comprises one or more annular positioning discontinuity complementary to the one or more annular positioning discontinuity on the barrel, which together control distal motion of the barrel relative to the sleeve. The quantity of flush solution is in the chamber between the stopper and distal wall of the barrel.

In some embodiments, the distal end annular channel of the cap further comprises a straight inner wall and an outer wall that is threaded to complement the VAD, and the distal end annular channel extends less than the length of the cap.

In one or more embodiments, the proximal end annular channel of the cap further comprises a straight outer wall and an inner wall that is releasably attached to the barrel, and the proximal end annular channel extends less than the length of the cap. In detailed embodiments, the proximal end annular channel of the cap is attached to the barrel by one or more of an interference fit and a threaded connector.

In some embodiments, the profiled center passageway of the cap extends the entire length of the cap to establish fluid connection between the barrel and the VAD, and the profile of the center passageway is undercut near the proximal end to complement the profile of external surface of stopper tip. In detailed embodiments, the profiled center passageway of the cap is coated with an antimicrobial agent.

In one or more embodiments, the stopper or any portion of the stopper is detachable from the stopper and capable of being embedded into the VAD. In some embodiments, the stopper has a cavity to hold a stopper tip by one or more of a threaded connection and an interference fit. In detailed embodiments, the profile of the distal end of the stopper tip is configured to complement the profile of the center passageway of the cap and create an interference fit therewith sufficient to retain the stopper tip within the VAD after the flush syringe assembly is removed. In specific embodiments, the stopper tip is threadably attached to stopper using threads on the stopper tip that complement those on the VAD allowing both to be removed in one motion by the practitioner.

In some embodiments, the annular positioning discontinuities on the barrel comprise two annular positioning ridges, a distal annular positioning ridge and a proximal annular positioning ridge and the discontinuity on the sleeve comprises a groove configured to interact with the annular positioning ridges on the barrel.

In one or more embodiments, the outside surface of the barrel further comprises one or more linear discontinuity spaced around the barrel that run along a length of the barrel and engage with a corresponding discontinuity on the inside surface of the sleeve.

Additional embodiments of the invention are directed to methods of sterilizing a VAD connector prior to flushing. A protective cover is removed from the distal end of the syringe assembly as described herein to expose a disinfectant contained at the distal end of the syringe assembly. The disinfectant is applied to the VAD connector and the sleeve is depressed to eject the disinfecting system, or disinfectant carrier and hub.

Further embodiments of the invention are directed to methods of preventing contamination of a VAD connector while being worn by a patient. The method comprising leaving a Luer cap containing an embedded plunger tip connected to the VAD connector to protect the VAD connector from contact with bacteria or other contaminants.

BRIEF DESCRIPTION OF THE DRAWINGS

So that the manner in which the above recited features of the invention are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

FIG. 4A shows a distal perspective view of a cap in accordance with one or more embodiments of the invention;

FIG. 4B shows a proximal perspective view of a cap in accordance with one or more embodiments of the invention;

FIG. 5 shows a cross-sectional view of a cap in accordance with one or more embodiments of the invention;

FIG. 18 shows a cross-sectional view of a flush syringe assembly after retracting the sleeve to disengage the disinfecting system in accordance with one or more embodiments of the invention;

FIG. 19 shows an expanded cross-sectional view of the flush syringe assembly and the disinfecting system after disengagement in accordance with one or more embodiments of the invention;

FIG. 21 shows a cross-sectional view of a VAD being connected to the flush syringe assembly in accordance with one or more embodiments of the invention;

FIG. 22 shows an expanded cross-sectional view of the VAD connected to the flush syringe assembly in accordance with one or more embodiments of the invention;

FIG. 23 shows a cross-sectional view of the flush syringe assembly connected to the VAD in the initial position in accordance with one or more embodiments of the invention;

FIG. 24 shows a cross-sectional view of the flush syringe assembly connected to the VAD during flushing in accordance with one or more embodiments of the invention;

DETAILED DESCRIPTION

Figure 1:
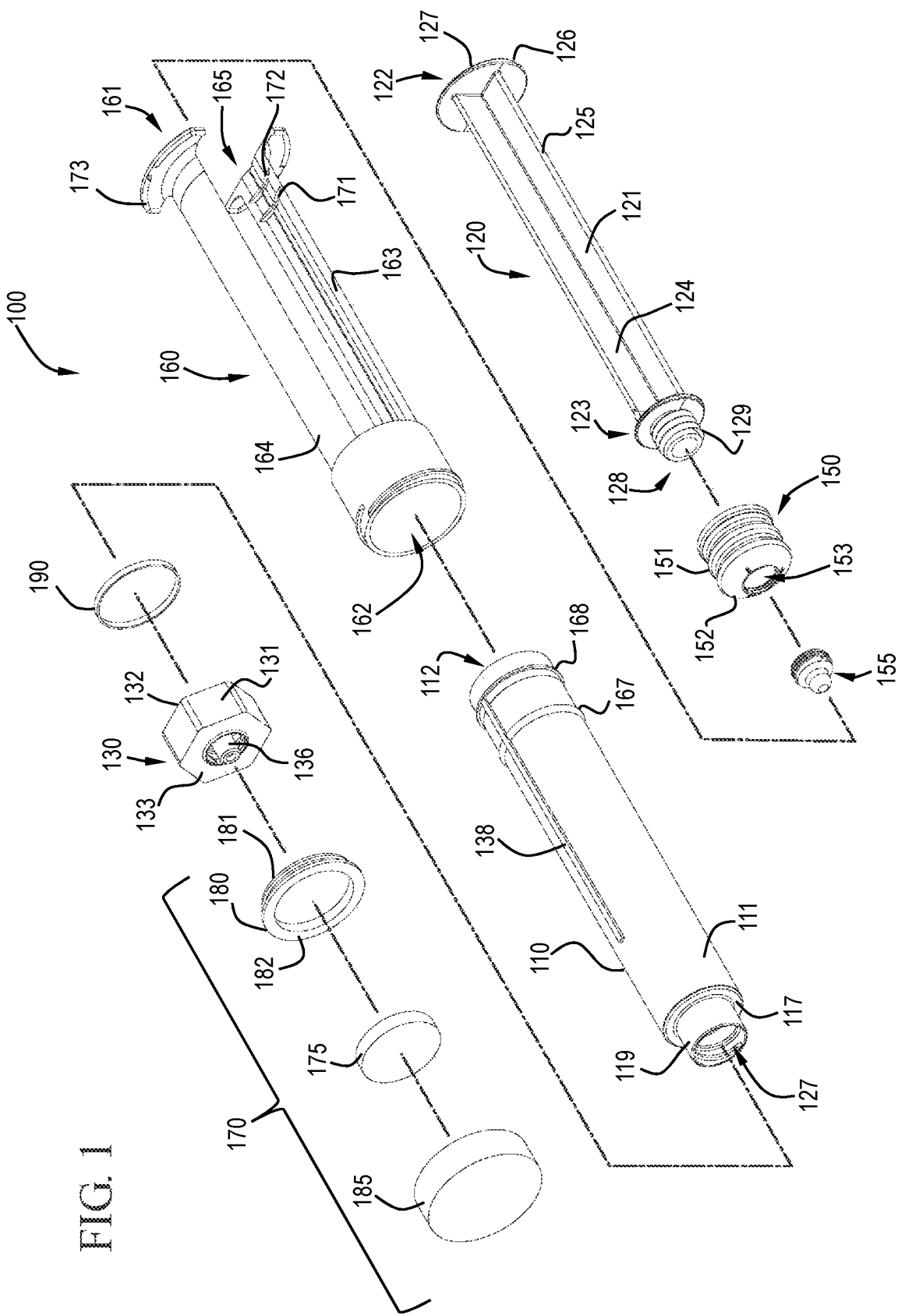
FIG. 1 shows a perspective view of a flush syringe assembly in accordance with one or more embodiments of the invention.

Before describing several exemplary embodiments of the invention, it is to be understood that the invention is not limited to the details of construction or process steps set forth in the following description. The invention is capable of other embodiments and of being practiced or being carried out in various ways.

Embodiments of the invention are directed to syringe assemblies with valves and plugs which allow for one or more of prevention of blood reflux, elimination of the need for catheter positive displacement connectors and protection of the IV connector by capping of the IV connector.

The devices may prevent blood reflux into IV catheter lumens, after the catheter flushing procedure, eliminate the need for IV catheter positive displacement connectors or valves and/or protect the IV connector from contamination by capping the IV connector. These systems have the potential to extend catheter dwell times, reduce the use of Cathflo® (t-PA, Alteplase), and cap IV connectors to reduce the risk for connector inlet port bacterial colonization. One or more embodiments are directed to systems for disinfecting/cleaning connectors, flushing IV lines, preventing reflux, capping/sealing connector inlet port surfaces (e.g., to prevent microorganisms from entering IV lines or populate the connector inlet port surfaces).

The figures show embodiments of a syringe assembly comprising an integrated contamination-prevention device integrated with VAD connector flushing positioned so that the practitioner cannot forget to apply disinfectant. Those skilled in the art will understand that the syringe assembly shown is merely one embodiment and that the syringe assembly can have different structures and components. Accordingly, one or more embodiments of the invention are directed to flush syringe assemblies 100 including a barrel 110, an elongate plunger rod 120, a cap 130 and a valve 140.

Figure 2:
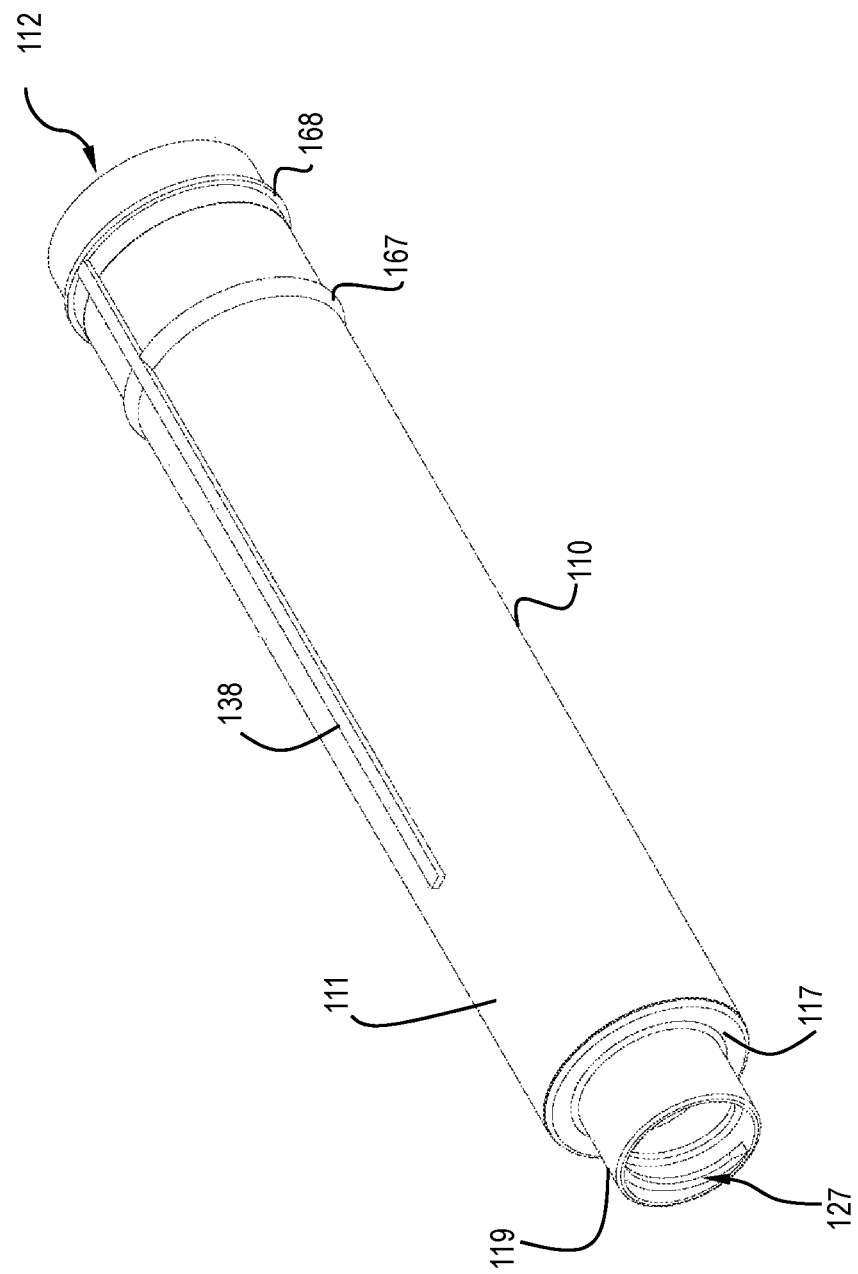
FIG. 2 shows a perspective view of a syringe barrel in accordance with one or more embodiments of the invention.
Figure 3:
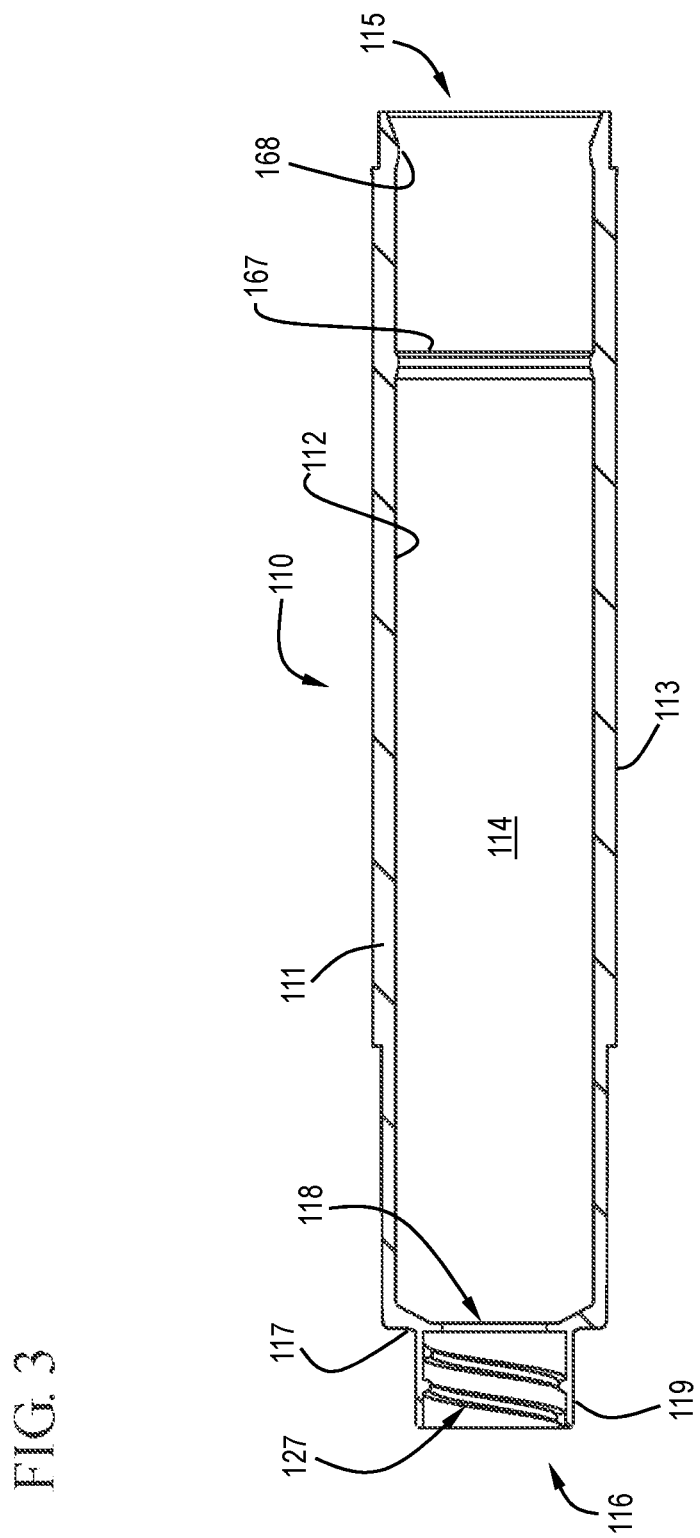
FIG. 3 shows a cross-sectional side view of a syringe barrel in accordance with one or more embodiments of the invention.

Referring to FIGS. 2 and 3, the barrel 110 has a side wall 111 with an inside surface 112 defining a chamber 114 for retaining a fluid, an outside surface 113, an open proximal end 115 and a distal end 116. The distal end 116 includes a distal wall 117 with an passageway 118 therethrough in fluid communication with the chamber 114 allowing a fluid within the chamber 114 to exit the chamber through the passageway 118. In some embodiments, the barrel 110 does not include a flange for providing opposing force to the direction of movement of the plunger rod.

The outside surface 113 of the barrel 110 can be smooth or textured depending on the desired frictional quality of the resulting syringe assembly 100. For example, a textured outside surface 113 may offer the user a more stable and secure grip than a smooth surface. Additionally, the roughness or frictional feel of the outside surface 113 may be modified by the chemical composition of the material used in the syringe barrel 110.

The barrel 110 may also include features to control the linear movement of the barrel relative to a sleeve and to restrict their relative rotational movement. To control the linear movement of the barrel 110 relative to the sleeve, the barrel may include at least one annular positioning ridge 167, 168 on the outside surface. In the embodiment shown in FIG. 1, the barrel includes a proximal annular positioning ridge 168 and a distal annular positioning ridge 167. To control the linear movement, in some embodiments, annular ridges 167, 168 can engage with corresponding features on the inside surface of the sleeve. In some embodiments, the distal annular positioning ridge 167 positions the sleeve 160 during shipping of the flush syringe assembly. In one or more embodiments the proximal annular positioning ridge 168 stops the movement of the sleeve 160 relative to the barrel 110 after the disinfecting system is ejected.

To control the rotational movement of the sleeve 160 relative to the barrel 110, the barrel may contain a ridge 167 that can extend, for example, substantially from the proximal end 115 of the barrel 110 toward the distal end 116. The ridge 167 can extend along any portion of the length of the barrel 110. The ridges 138 can start and stop at any point along the length of the barrel 110. The ridges 138 (or ridge) can be sized to engage with a corresponding groove 177 on the inside surface 163 of a sleeve 160 to facilitate alignment of the barrel 110 with the sleeve 160 while the plunger is being depressed.

While the embodiments have been described and shown as having a ridge extending from the barrel to interact with a groove in the sleeve, it will be understood by those skilled in the art that these features can be reversed. For example, there may be a least one annular positioning groove on the barrel that interacts with at least one annular positioning ridge on the inside surface of the sleeve. In some embodiments, there are at least one annular positioning discontinuity on the barrel and at least one complementary annular positioning discontinuity on the inside surface of the sleeve. Similarly, the barrel may contain a linear discontinuity that extends along a length of the barrel that interacts with a complementary discontinuity on the inside surface of the sleeve.

The barrel 110 may also include a tip 119 which extends distally from the barrel 110. The tip 119 can have an outer diameter that is different from or the same as the outer diameter of the rest of the barrel 110. For example, as shown in the Figures, the outer diameter of the tip 119 has a smaller outer diameter than the barrel portion that is proximal of the tip 119. The tip 119 of the barrel 110 may include a Luer slip connection (not shown) or a locking Luer type collar concentrically surrounding the tip 119 or within the tip. The tip 119 shown in the Figures is a Luer lock type connector 127 on the inside of the tip.

Figure 9:
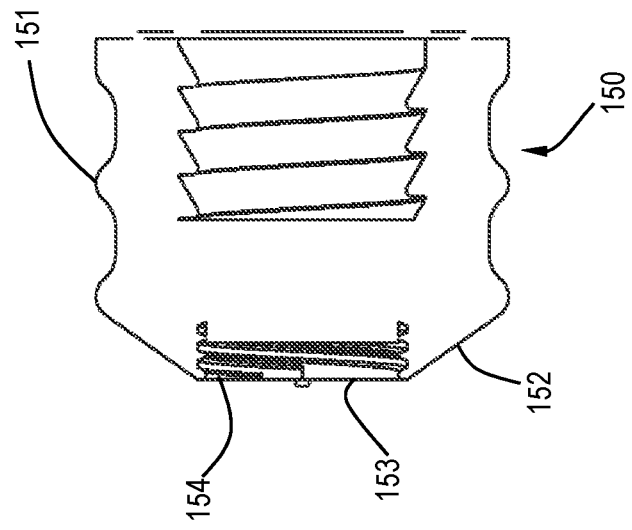
FIG. 9 shows a cross-sectional view of a stopper in accordance with one or more embodiments of the invention.
Figure 8:
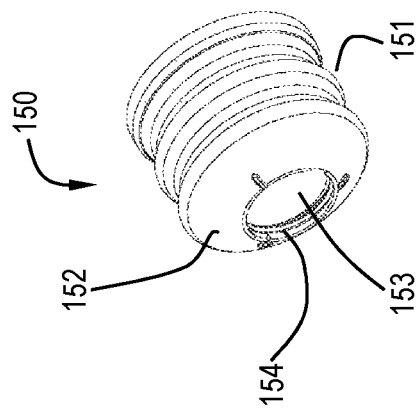
FIG. 8 shows a distal perspective view of a stopper in accordance with one or more embodiments of the invention.

An elongate plunger rod 120 is disposed within the barrel 110, as shown in FIGS. 1 and 8 to 9. The plunger rod 120 includes an elongate body portion 121 with a proximal end 122 and a distal end 123.

The elongate body portion 121 of the plunger rod 120 has an axial length extending from the proximal end 122 to the distal end 123. The body portion 121 may include a single beam or features, which may have cylindrical or other shapes. As shown in the Figures, the body portion 121 is formed by two perpendicularly intersecting beams 124, 125. The beams may have a plus-shaped or cruciform cross-section. In the embodiment shown, the two intersecting beams 124, 125 intersect to form an outside surface outlining four quadrants that face the inside surface 112 of the barrel 110 and extend along the axial length from the proximal end 122 to the distal end 123 of the plunger rod 120. While the drawings show embodiments of the plunger rod with a cruciform cross-section, it will be understood by those skilled in the art that the shape and/or cross-section of the plunger rod can be any suitable shape or cross-section and that the embodiments of the invention are not limited to the shapes shown in the drawings.

The plunger rod 120 may also include a thumbpress 126 at the proximal end 122 of the elongate body portion 121. The shape of the thumbpress 126 can vary depending on the desired usage of the flush syringe assembly 100. The thumbpress 126 shown in the drawings is round, but it will be understood by those skilled in the art that this is merely representative of one possible shape. Other shapes include, but are not limited to, square, rectangular, triangular, oval, pentagonal, hexagonal and cruciform. The shape of the thumbpress 126 in some embodiments substantially matches the shape of the elongate body portion 121 of the plunger rod 120, the barrel 110 or other components.

In some embodiments, the thumbpress has a plurality of ridges 127 thereon. The ridges 127 may enhance the ability of the user to press the plunger rod 120 distally with respect to the barrel 110 by providing a surface with an increased coefficient of friction. The shape of the ridges 127 or the ridge pattern can be changed depending on the desired usage of the plunger rod 120. For example, the ridges 127 can be a series of parallel lines, or curved in a design. In one or more embodiments, the ridges 127 are shaped to form a logo. The ridges 127 can be integrally formed with the plunger rod 120 or can be separate pieces that are attached to the plunger rod. The surface of the ridges 127 can be textured differently from the plunger rod or can be the same. Ridges 127 with a textured surface may provide a greater increase in the coefficient of friction than smooth ridges.

A stopper 150 can be connected to the distal end 123 of the plunger rod 120. The shape and size of the stopper 150 can be any suitable shape or size depending on, for example, the shape and size of the barrel 110 and plunger rod 120. The plunger rod 120 is slidably positioned in the barrel 110 so that the stopper 150 is in fluid-tight contact with the inside surface 112 of the barrel 110 and so that distal movement of the plunger rod 120 relative to the barrel 110 causes the stopper 150 to push the fluid out of the barrel 110. In some embodiments, the stopper 150 is slidably positioned in fluid-tight contact with the inside surface 112 of the barrel 110 for driving fluid out of the chamber 114 by movement of the stopper 150 relative to the barrel 110.

The plunger rod 120 shown in FIG. 1 includes a connector 128 on the distal end 123 of the plunger rod 120. The connector 128 shown includes screw threads 129 to which a stopper 150, or other component, can be attached by cooperative interaction with screw threads on the stopper 150. It will be understood by those skilled in the art that there are other types of connectors 128 besides screw threads 129. For example, the connector may include one or more axially spaced rings about the outside surface of the connector 128. The spaced rings provide can cooperatively interact with one or more grooves in the stopper 150 to affix the stopper 150 to the distal end 123 of the plunger rod 120.

Figure 10:
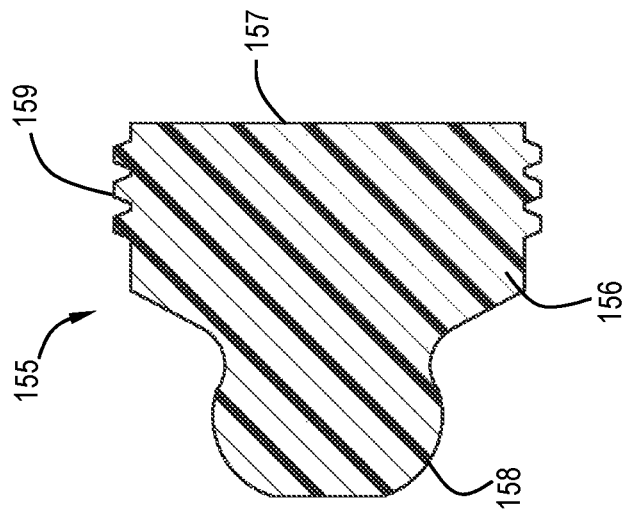
FIG. 10 shows a distal perspective view of a detachable stopper tip in accordance with one or more embodiments of the invention.
Figure 11:
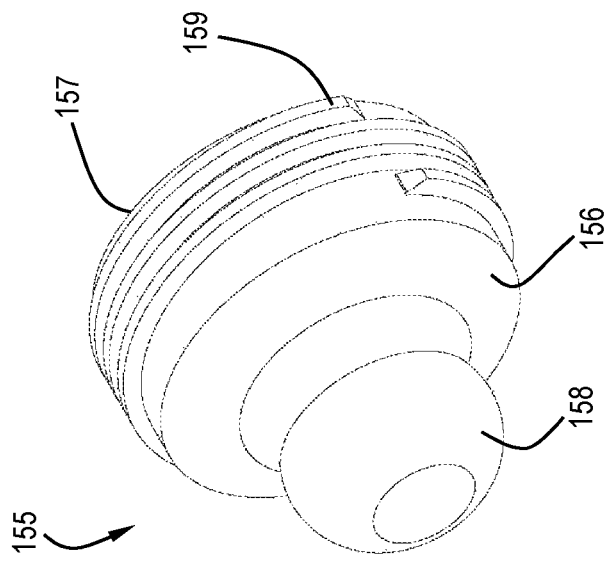
FIG. 11 shows a cross-sectional view of a detachable stopper tip in accordance with one or more embodiments of the invention.

The stopper 150 can be connected to the distal end 123 of the elongate plunger rod 120 by any suitable means. In some embodiments, the stopper 150 is connected by a mechanical connection such as interaction of complementary screw threads, as shown in FIG. 9, and press-fit connections. The stopper 150 can be a single piece or multiple pieces. In some embodiments, the stopper 150 is multiple pieces having a stopper body 151 and a detachable stopper tip 155, as shown in FIGS. 1, 10 and 11. In one or more embodiments, the stopper 150 includes a conically-shaped distal surface 152 and the barrel 110 includes a conically-shaped inside surface at the distal wall 117. Those skilled in the art will understand that conically-shaped can also include frustoconical shapes. In some embodiments, the stopper 150 includes a shape that is complementary to the shape of the distal end of the barrel 110 so that the stopper 150 is effective to expel the contents of the chamber 114 through the distal end 116 of the barrel 110. The stopper 150 may be slidably positioned in fluid-tight engagement with the inside surface 112 of the barrel 110 for drawing fluid into and driving fluid out of the chamber 114. If the syringe assembly is prefilled from the manufacturer, the stopper 150 need not be used for or able to draw fluid into the barrel 110.

The stopper 150 may be made of any material suitable for providing a seal with the inside surface 112 of the barrel 110. For example, the stopper 150 may be made of thermoplastic elastomers, natural rubber, synthetic rubber or thermoplastic materials and combinations thereof. The stopper 150 may be integrally formed or composed of separate components of the same or different materials joined together. The plunger rod 120 may be made of material which is more rigid than the stopper 150 such as polypropylene, polyethylene and the like. Materials should be chosen to be compatible with the procedure being used.

As shown in FIGS. 8 and 9, the stopper may include a cavity 153 in the distal end to allow a detachable stopper tip 155 to be connected thereto. The detachable stopper tip 155 can be connected to the stopper 150 by any suitable connection including, but not limited to, screw threads or a interference fit. The stopper 150 shown in FIGS. 8 and 9 includes screw threads 154 in the cavity 153 which can cooperatively interact with the detachable stopper tip 155.

As shown in FIGS. 10 and 11, the detachable stopper tip 155 includes a body 156 with a proximal end 157 and distal end 158. The proximal end 157 of the tip 155 shown in the Figures includes screw threads 159 which can interact with the complementary threads on the stopper 150. It will be understood by those skilled in the art that the cooperative nature of the screw threads hold the detachable stopper tip 155 to the stopper 150 during normal use and can be overcome to release the detachable stopper tip 155 from the stopper 150 when needed, as described further below.

The distal end 158 of the detachable stopper tip 155 can be any suitable shape. For example, as shown in FIG. 11, the distal end 158 of the tip 155 can be shaped like a tow hitch with a region of smaller diameter to form a tight connection with a mating surface. As described further below, in use, the larger diameter end of the tip 155 passes into the VAD, or other connection and becomes wedged in place by the smaller diameter portion, so that upon retraction of the stopper, the screw threads of the tip are overcome, releasing the tip from the stopper and leaving the tip wedged in the VAD.

In some embodiments, the distal end 158 of the detachable stopper tip 155 comprises a profiled tip. The profiled tip can be sized and shaped to be seatable within the VAD when the plunger rod is fully depressed. For example, the detachable stopper tip can be seated in a correspondingly shaped undercut region 192 in the cap 130 which can then be left on the end of the vascular access device, thereby sealing the VAD with the combined cap 130 and detachable stopper tip 155. The detachable stopper tip 155 with the profiled distal end 158 is configured to complement the profile of the center passageway 134 of the cap 130 to create an interference fit therewith sufficient to retain the detachable stopper tip within the VAD after the flush syringe assembly 100 has been removed. For example, the center passageway 134 may include the undercut region 192 described with reference to FIG. 5.

In one or more embodiments, the stopper 150 or a portion of the stopper (e.g., the detachable stopper tip 155) can be detached from the stopper 150 or from the plunger rod 120 and can be embedded into the VAD, or into a suitable undercut region 192 in the cap 130.

The cap 130 of various embodiments includes a body 131 with a proximal end 132, a distal end 133 and a tip 136 extending distally from the distal end 133. The distal end 133 and the proximal end 132 define the length of the cap 130. FIGS. 4A, 4B and 5 show a distal view, a proximal view and a cross-sectional view, respectively, of a cap 130 in accordance with one or more embodiments of the invention. Upon assembly, the proximal end 132 of the cap 130 is adjacent the distal end 116 of the barrel 110. The cap 130 comprises a passageway 134 extending through the tip 136 and the body 131 of the cap 130. The passageway 134 allows for fluid communication between the chamber 114 of the barrel 110 and the device attached to the distal end 133 of the cap 130. Thus allowing a fluid within the chamber 114 to be expelled through the distal end of the barrel 110 and through the cap 130 from the distal end 133 to the proximal end 132.

The cross-sectional shape of the cap 130 can be any suitable shape including, but not limited to, triangular, square, pentagonal, hexagonal, heptagonal, octagonal, symmetric or non-symmetric polygonal. The shape of the cap 130 can provide a comfortable feel for the user and enhanced gripping ability to allow the user to easily connect or disconnect the cap from the barrel 110. In some embodiments, the cap 130 is irregularly shaped. As used in this specification and the appended claims, the term "irregularly shaped" means that the cross-sectional shape provides a surface or edge that is detrimental to free rotation about the cross-section. For example, a hexagon or oval shape would be considered "irregular".

As shown in FIG. 5, the distal end of the passageway 134 can be profiled to cooperatively interact with a detachable stopper tip to form a seal. This profiled area may be referred to as an undercut region 192, but it will be understood by those skilled in the art that the profile is not limited to undercut profiles. In some embodiments, the profiled center passageway of the cap 130 extends the entire length of the cap 130 to establish fluid connection between the barrel 110 and the VAD and the profile of the center passageway is undercut near the proximal end to complement the profile of an external surface of the stopper tip or the detachable stopper tip.

The cap 130 includes a Luer connector 135 on the distal end 133, as shown in FIGS. 4A and 5. The Luer connector 135 allows the cap 130, and any connected barrel 110, to be releasably connectable to a vascular access device (VAD) or other suitable device with a matching Luer type connection. The Luer connector 135 shown is a Luer-Lok type connector comprising screw threads. However, the Luer connector can also be a Luer-slip type connector without screw threads. In some embodiments, the distal end 133 of the cap 130 includes an annular channel that releasably attaches to the VAD and the proximal end 132 has an annular channel that releasably attaches the cap 130 to the barrel 110. Either of the annular channels can include at least one screw thread adapted to allow the cap to be screwed onto one or more of the barrel 110 and the VAD. In some embodiments, the cap can engage complementary threads on the VAD or engages the VAD with an interference fit.

Additionally, the proximal end 132 of the cap 130, as shown in FIGS. 4B and 5, is releasably attachable to the barrel 110 via a suitable connector 137. Suitable connectors 137 include, but are not limited to, Luer slip and Luer-Lok type connectors. FIG. 4B shows the proximal end 132 of a cap 130 in accordance some embodiments. The connector 137 shown in FIG. 4B is a Luer-Lok type connector which includes screw threads.

The passageway 134 can be smooth, rough, coated or uncoated. In some embodiments the inner surface of the passageway 134 is coated with an antimicrobial agent.

In some embodiments, the cap 130 includes a distal end annular channel 231 comprising a straight inner wall 232 and an outer wall 233 that is threaded to complement threads on the VAD or form an interference fit. The distal end annular channel 231 can extend less than the length of the cap 130. For example, the distal end annular channel 231 can extend less than about 90% of the length of the cap 130, or less than about 80% of the length of the cap 130, or less than about 70% of the length of the cap 130, or less than about 60% of the length of the cap 130, or less than about 50% of the length of the cap 130.

In some embodiments, the cap 130 includes a proximal end annular channel 235 which comprises a straight outer wall 236 and an inner wall 237 that is releasably attached to the barrel 110. The proximal end annular channel 235 can extend less than the length of the cap 130. For example, the proximal end annular channel 235 can extend less than about 90% of the length of the cap 130, or less than about 80% of the length of the cap 130, or less than about 70% of the length of the cap 130, or less than about 60% of the length of the cap 130, or less than about 50% of the length of the cap 130. The proximal end annular channel 235 can be connected to the barrel by one or more of threaded connections or by an interference fit.

Figure 6:
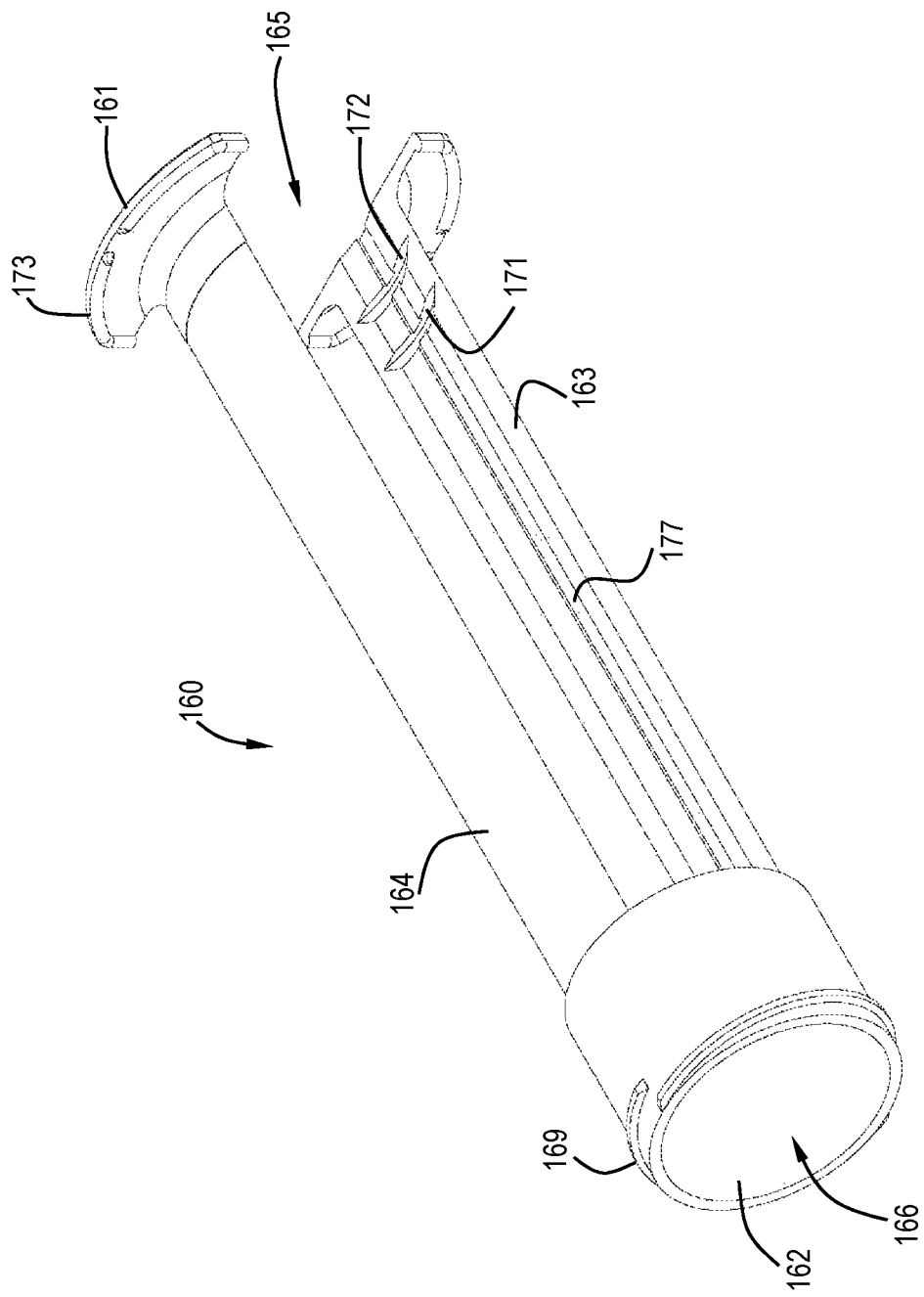
FIG. 6 shows a perspective view of a sleeve in accordance with one or more embodiments of the invention.
Figure 7:
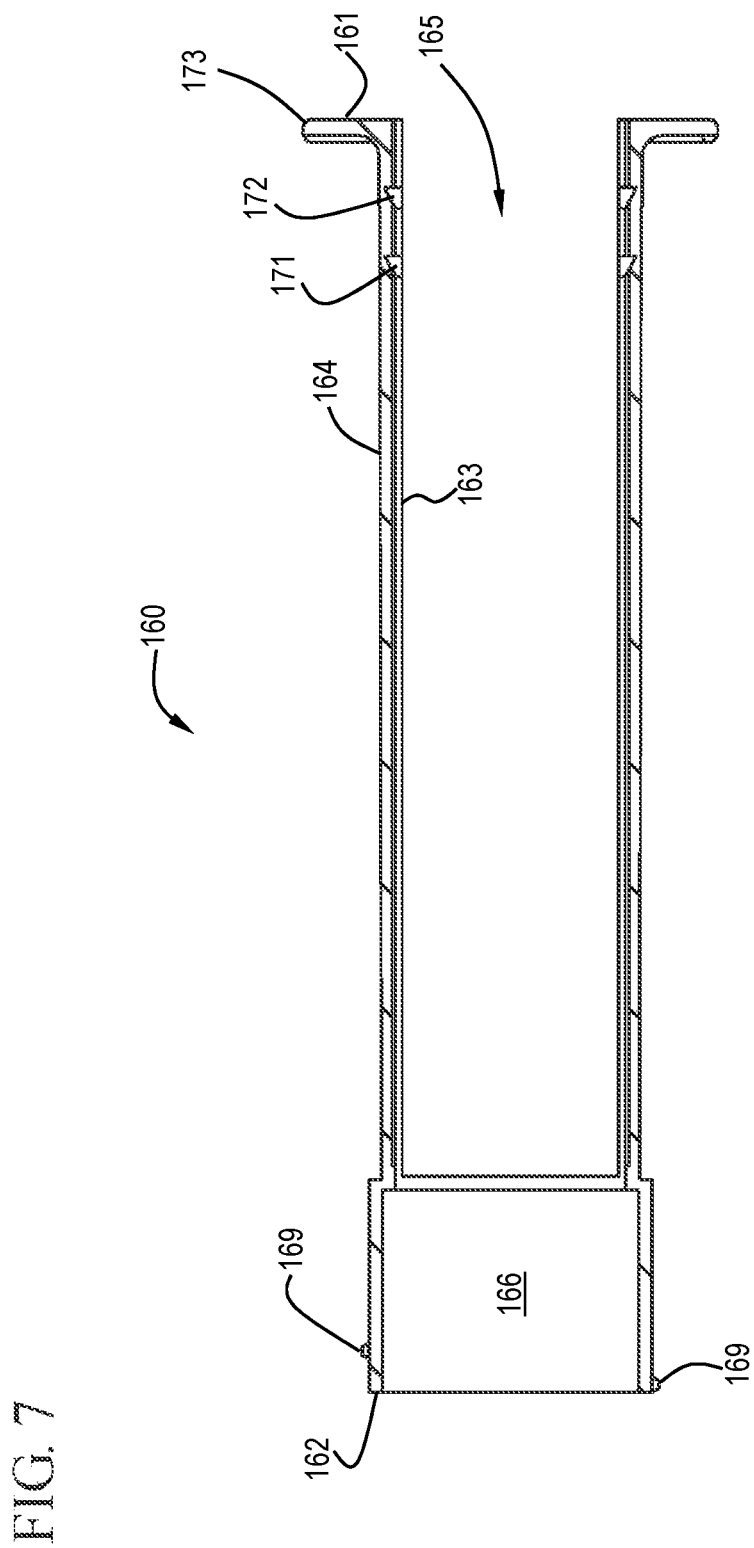
FIG. 7 shows a cross-sectional view of a sleeve in accordance with one or more embodiments of the invention.

In some embodiments, the flush syringe 100 includes a sleeve 160 and a disinfecting system 170. As shown in FIGS. 1 and 6 to 7, the sleeve 160 is coaxial with and external to the barrel 110 and has a proximal end 161, a distal end 162, an inside surface 163 and an outside surface 164. The sleeve 160 can slide from a distal position to a proximal position relative to the barrel 110. The sleeve of some embodiments covers the cap 130 prior to use of the flush syringe assembly 100. The sleeve 160 may include a cavity 166 on the distal end 162 that is sized to enclose the cap 130. The flush syringe assembly 100 can be packaged with the sleeve 160 already in place or as a separate component. The sleeve can be used to disengage the disinfectant carrier 175, described below, and/or cover the cap 130 until flushing of the vascular access device connection is complete.

The shape of the sleeve 160 can vary depending on the use of the device. For example, as shown in the drawings, the sleeve 160 is round, like the barrel 110, and sized to fit around the barrel 110. The sleeve 160 has one or more cutouts 165 which allow visibility of the barrel 110 and the contents therein. The sleeve can have any number of cutouts 165 including, but not limited to, one, two, three and four cutouts. For example, the sleeve 160 shown in the Figures has two cutouts 165 on opposite sides of the sleeve 160. Without being bound by any particular theory of operation, it is believed that the cutouts provide greater visibility of the contents of the barrel and/or increase the flexibility of the sleeve to allow the sleeve to more easily conform to the outside surface of the barrel and/or to facilitate motion of the barrel relative to the sleeve.

The distal end 162 of the sleeve 160, in some embodiments, has a threaded portion 169 which can be used to attach the disinfecting system 170. While a threaded portion 169 is shown, it will be understood by those skilled in the art that other attachment mechanisms can be used including, but not limited to, interference fits.

In some embodiments, the inside surface 163 of the sleeve 160 comprises one or more grooves 177 that engage with corresponding ridge (or ridges) 138 on the outside surface of the barrel 110 to facilitate alignment of the barrel and sleeve while the plunger is depressed. In one or more embodiments, the plunger is of sufficient length relative to the sleeve and the barrel so that when the plunger is fully depressed, after flushing solution has been pushed through the VAD, the sleeve retracts, thereby exposing the cap.

In some embodiments, the sleeve is external to the barrel 110 and has an open proximal end 161 containing at least one flange 173 and an open distal end 162 defining a recess 166 with an inner surface to contain the cap. In detailed embodiments the recess 166 is irregularly shaped to prevent rotation of the cap relative to the sleeve. For example, the recess 166 may have a hexagonal shape matching a hexagonal shaped cap.

In one or more embodiments, the sleeve 160 comprises two linear grooves 177 positioned on opposite sides (about 180° apart) that run substantially from the proximal end of the sleeve toward the distal end of the sleeve. The linear grooves 177 can be configured to interact with the ridges 138 on the outside surface of the barrel 110.

Referring to FIG. 1, the disinfecting system 170 comprises a disinfectant on a disinfectant carrier 175 contained in a hub 180. The hub 180 has a proximal face 181 and a distal face 182 and is sized to fit within the cover 185. The hub 180 can be made from any suitable material including, for example, a thermoplastic material. The distal face 182 of the hub 180 can be substantially flat or have a recessed section.

The disinfectant carrier 175 can be any suitable material capable of carrying and providing a disinfecting medium to the vascular access device. The disinfectant carrier 175 can be adhered to the distal face 182 of the hub 180 by any suitable means including, but not limited to, medical grade adhesive or tape. In one or more embodiments, the disinfectant carrier 175 is sized to fit within a recess in the distal face 182 of the hub 180 and can be secured thereto by either adhesive or by an interference fit.

The disinfectant can be any suitable composition capable of cleaning the connection to the vascular access device. In one or more embodiments, the disinfectant carrier 175 is saturated with, or wetted with, a solution comprising the disinfectant. In some embodiments, the disinfectant comprises one or more disinfecting materials such as alcohol and antiseptic gels. The disinfectant carrier 175 of some embodiments includes sufficient disinfectant to disinfect the VAD's inlet port.

In some embodiments, the disinfecting system 170 further comprises a removable cover 185. The removable cover 185 is capable of protecting the disinfecting system prior to use including the disinfectant carrier 175. The removable cover 185 can be connected to either the hub 180 with the sleeve 160 by one or more of an interference fit or through engagement of complement retreads.

The disinfecting system 170 can be assembled on the distal end of the flush syringe assembly 100 in a number of configurations. In one or more embodiments, the disinfecting system 170 is arranged such that the disinfectant carrier 175 is fitted within a recess on the distal face 182 of the hub 180. The proximal face 181 of the hub 180 is positioned adjacent the distal end 133 of the cap 130 and is held in place by engagement with the inside surface of the distal end 162 of the sleeve 160 by either complementary screw threads or an interference fit. The cover 185 is positioned over the disinfectant carrier 175 and the hub 180 and is attached to the distal end 162 of the sleeve 160 by one or more of complement or the screw threads or interference fit. In one or more embodiments, the disinfecting system 170 is attached to the distal end 162 of the sleeve 160 by an interference fit. In some embodiments, the disinfecting system 170 is attached to the distal end 162 of the sleeve 160 by engagement of complementary threads.

In one or more embodiments, the outside surface 113 of the barrel 110 includes a least one annular ridge 167, as shown in FIGS. 1 and 2. The annular ridge 167 is sized to provide a hindrance to spontaneous movement of the sleeve 160 relative to the barrel 110. The hindrance can be provided by, for example, an interference fit or cooperative interaction between a complementary feature 171 on the inside surface 163 of the sleeve 160. In some embodiments, the outside surface 113 of the barrel 110 includes at least two annular ridges 167, 168, as shown in FIGS. 1 through 8. Referring to FIG. 1, the annular positioning ridges comprise a distal annular positioning ridge 167 and a proximal annular positioning ridge 168. Also shown in FIG. 1, the sleeve 160 includes at least one annular positioning groove 171. In FIGS. 6-7, the sleeve 160 includes at least two annular positioning grooves: a distal annular positioning groove 171 and a proximal positioning groove 172. The annular positioning grooves 171, 172 are sized and positioned to help control the position of the sleeve 160 relative to the barrel 110 by engaging with the at least one annular positioning ridge 167, 168 on the outside surface 113 of the barrel 110.

In some embodiments, the sleeve 160 further comprises at least one flange 173 adjacent the proximal end 161 of the sleeve 160. The at least one flange 173 provides a region that can be gripped by the user to aide in the movement of the sleeve 160 relative to the barrel 110.

Some embodiments of the flush syringe assembly 100 further comprise a gasket 190. The gasket 190 can be sized to fit around the distal portion, including the tip 119, of the barrel 110 between the cap 130 and the distal wall 117 of the barrel 110. The gasket 190 can be made of any suitable material including, but not limited to, resilient rubber or plastic. The gasket 190 helps form a seal between the barrel 110 and the sleeve 160 and may have an outer diameter substantially equal to the outer diameter of the barrel 110 at the annular positioning ridges 167, 168. In some embodiments, there is an interference fit between the barrel 110 and the sleeve 160 without the need for a gasket 190.

Figure 12:
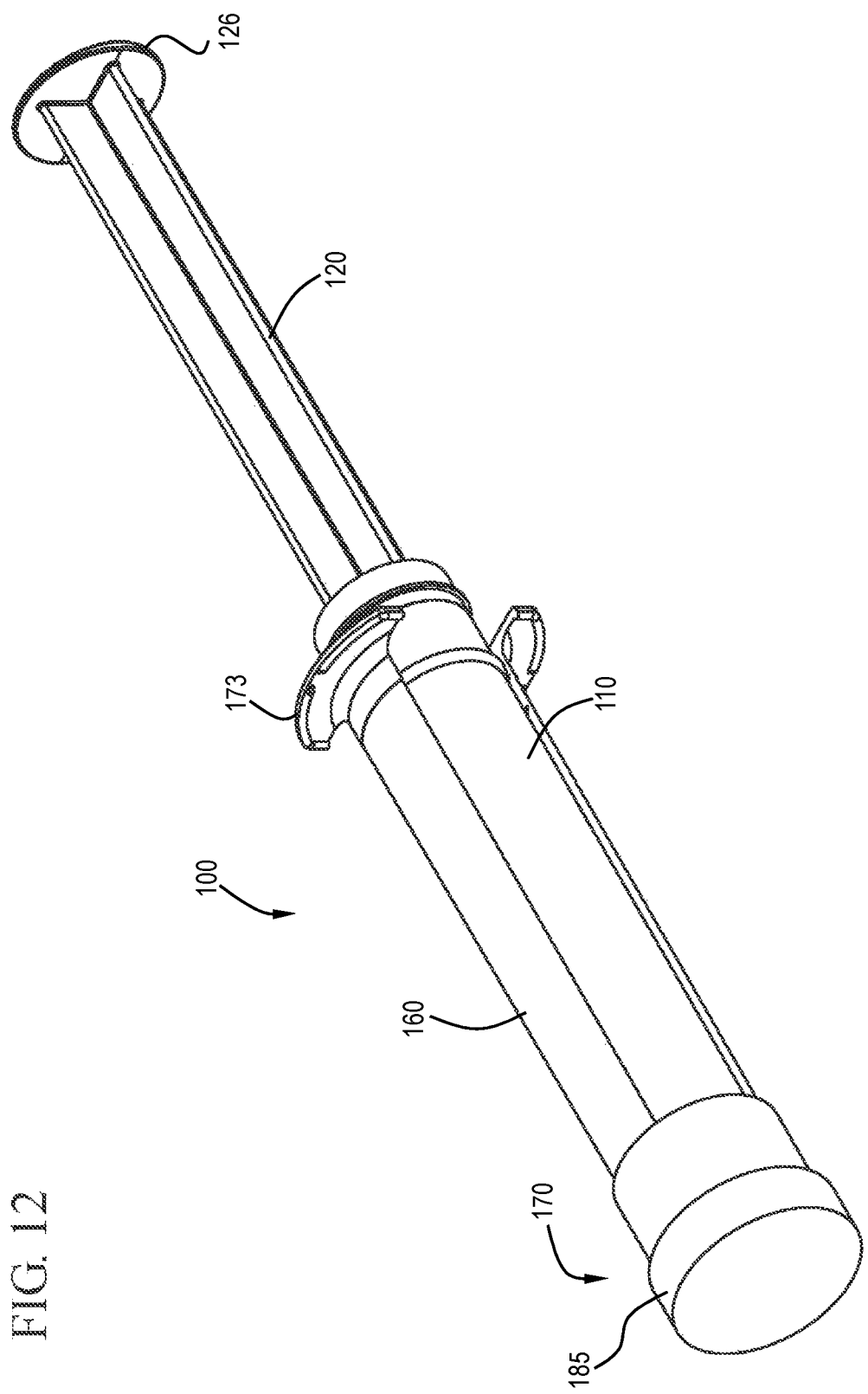
FIG. 12 shows a perspective view of a flush syringe assembly in accordance with one or more embodiments of the invention.
Figure 13:
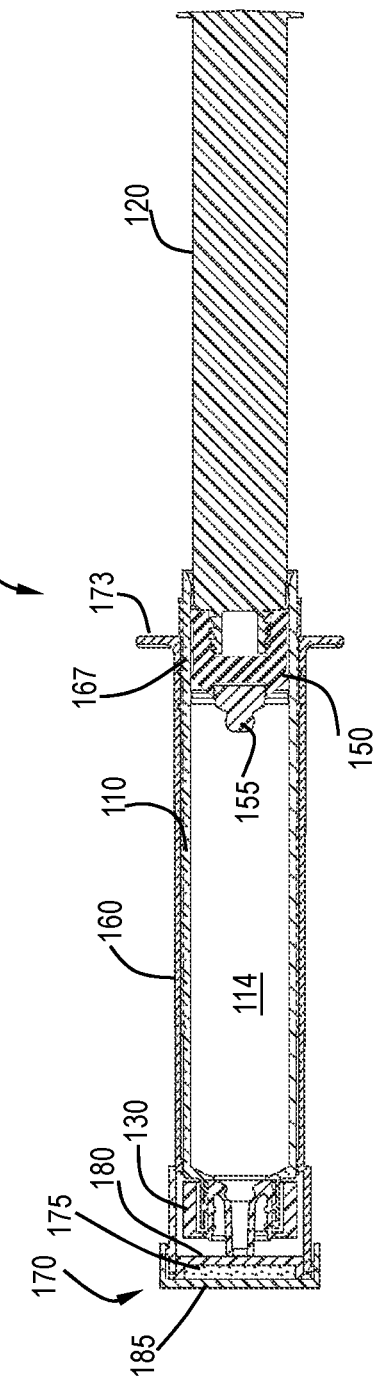
FIG. 13 shows a cross-sectional view of a flush syringe assembly in accordance with one or more embodiments of the invention.

The operation of a syringe assembly in accordance with one or more embodiments of the invention is now described with respect to FIGS. 12 through 32. FIGS. 12 to 13 show an embodiment of the flush syringe assembly 100 in initial state. The plunger rod 120 is positioned such that the stopper 150 is adjacent the proximal end 115 of the barrel 110. In this position, the chamber 114 has a maximum effective volume and can be either full of a medicament or empty. It will be understood by those skilled in the art that the flush syringe assembly 100 can be operated in the opposite fashion whereby in the initial state, the plunger rod 120 is positioned in the distal most position so that the cavity volume is minimized. Additionally, the plunger rod 120 can be initially positioned at any point between the proximal most position and the distal most position allowing for various uses and volumes of prefilled medicaments.

In the initial state, the disinfecting system 170 is connected to the distal end 162 of the sleeve 160 so that the hub 180 is connected to the sleeve with the disinfectant carrier 175 is positioned distally of the hub 180 and the cover 185 covers both the hub 180 and the disinfectant carrier 175. While other connections types can be used, the embodiment shown in the figures has the disinfecting system 170 connected to the sleeve 160 by cooperative interaction of screw threads on the outside of the sleeve 160 and the inside surface of the hub 180.

Figure 14:
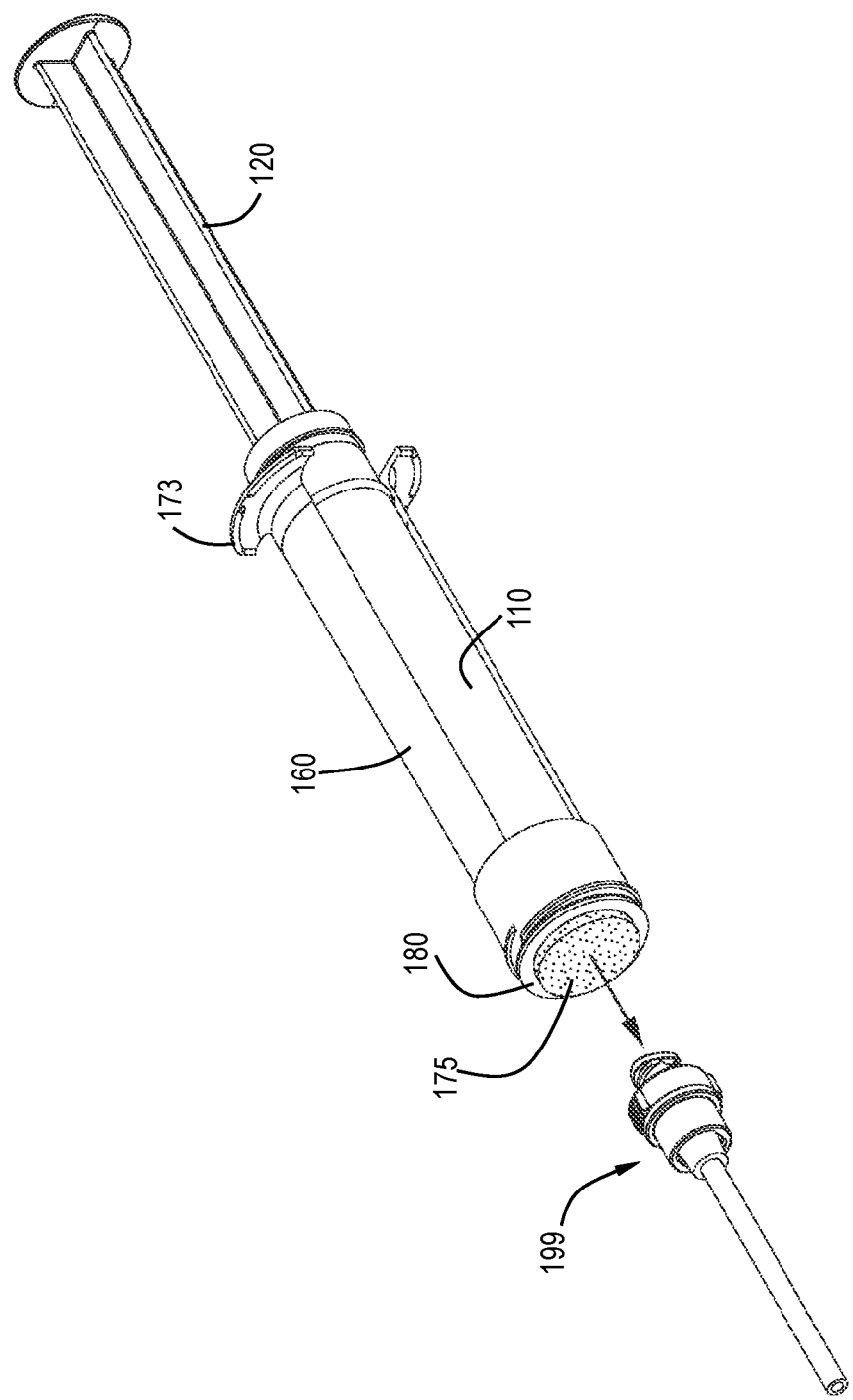
FIG. 14 shows a perspective view of a flush syringe assembly and a VAD prior to cleaning the VAD in accordance with one or more embodiments of the invention.
Figure 15:
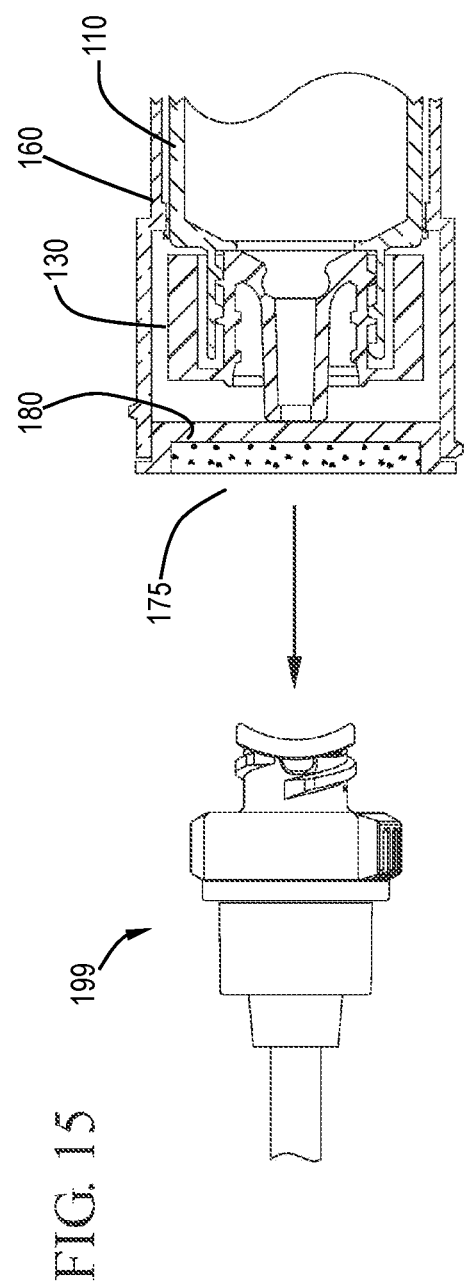
FIG. 15 shows an expanded cross-sectional view of a flush syringe assembly and a VAD prior to cleaning the VAD in accordance with one or more embodiments of the invention.
Figure 16:
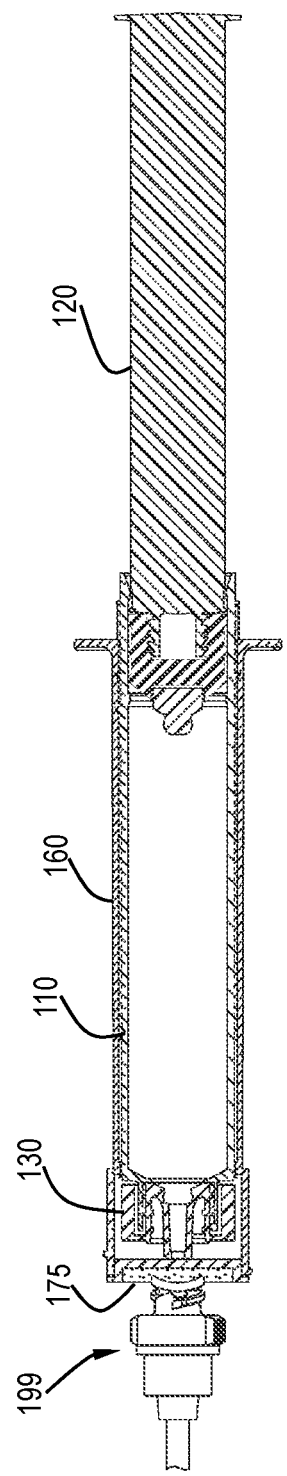
FIG. 16 shows a cross-sectional view of a flush syringe assembly cleaning a VAD in accordance with one or more embodiments of the invention.
Figure 17:
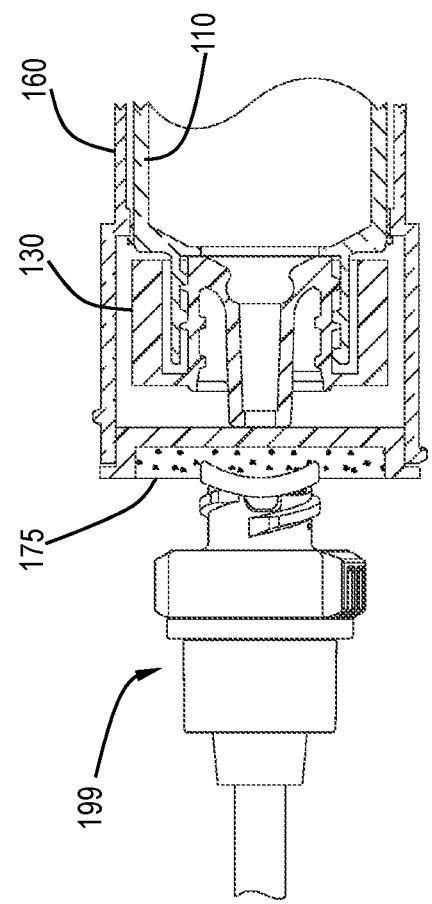
FIG. 17 shows an expanded cross-sectional view of the flush syringe assembly cleaning a VAD in accordance with one or more embodiments of the invention.

As shown in FIGS. 14 and 15, removal of the cover 185 exposes the disinfectant carrier 175 for use. The hub 180 and the distal face 182 of the hub 180 can be seen protruding slightly from the distal end 162 of the sleeve 160. With the disinfectant carrier 175 exposed, as shown in FIGS. 16 and 17, the user can clean the connection to the vascular access device 199 by contacting the disinfectant carrier 175 to the VAD 199.

Figure 20:
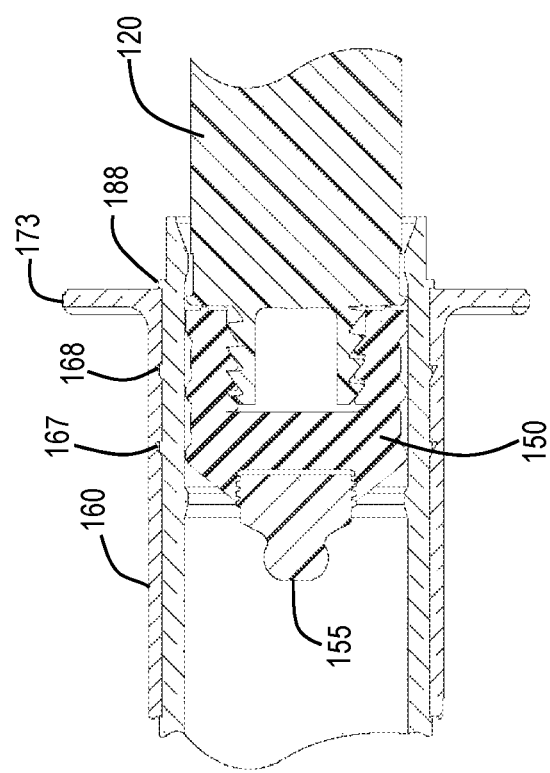
FIG. 20 shows an expanded cross-sectional view of a stopper and detachable stopper tip in accordance with one or more embodiments of the invention.

Referring to FIGS. 18 and 19, after cleaning the vascular access device 199, the user applies proximally directed force on the sleeve 160 relative to the barrel 110. The proximally directed force can be applied to the sleeve 160 with the aide of the flange 173 on the sleeve 160. This proximally directed force causes the sleeve 160 to slide proximally relative to the barrel 110 so that the sleeve slides from the distal position where the distal positioning ridge 167 is located to the proximal position where the proximal positioning ridge 168 is located. Proximal movement of the sleeve 160 relative to the barrel 110 is equivalent to distal movement of the barrel 110 relative to the sleeve 160. This distal movement of the barrel 110 relative to the sleeve causes the tip 136 of the cap 130 to press against the proximal face 181 of the hub 180, forcing the hub 180 to become disengaged from the distal end 162 of the sleeve 160. In the embodiment shown, the hub 180 is connected to distal end 162 of the sleeve 160 by an interference fit so that distally directed pressure on the hub 180 can cause the hub 180 to pushed out of the sleeve 160 without requiring a twisting motion. FIG. 19 shows the flush syringe assembly 100 after cleaning the vascular access device 199 and disengagement of the hub 180. The distal end of the cap 130 can be seen extending from the distal end 162 of the sleeve 160. FIG. 20 shows the proximal end of the barrel and sleeve with the sleeve 160 in the proximal position resting against stops 188 on the outside surface of the barrel. The stops 188 provide additional interference to prevent the sleeve from moving too far along the length of the barrel, thereby becoming disengaged from the barrel.

After the disinfecting system 170 has been removed from the distal end of the syringe assembly, the vascular access device 199, which is now clean, can be attached to the distal end 133 of the cap 130. FIGS. 21 to 23 show the flush syringe assembly after removal of the disinfecting system 170 and attachment of the VAD 199 to the cap 130. In FIG. 24, the stopper 150 and plunger rod 120 are shown at a point midway along the length of the barrel 110. This is representative of a flush syringe assembly in which part of the medicament or solution within the chamber 114 has been expelled through the cap 130 into the vascular access device 199.

Figure 25:
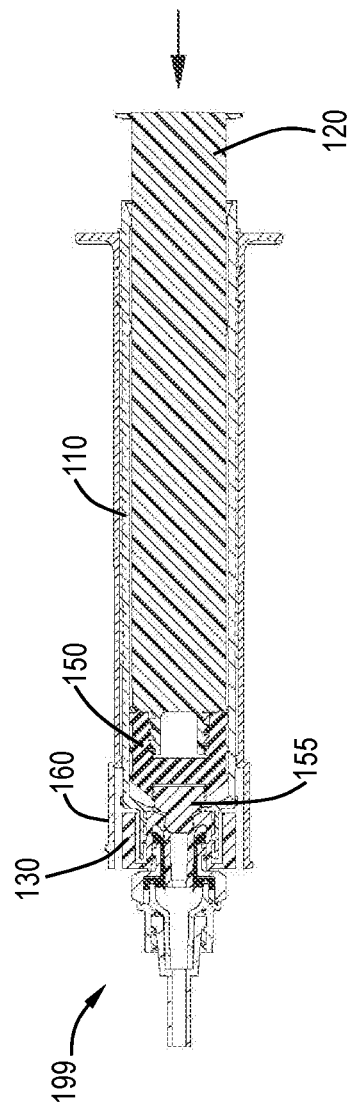
FIG. 25 shows a cross-sectional view of the flush syringe assembly connected to the VAD after flushing in accordance with one or more embodiments of the invention.
Figure 26:
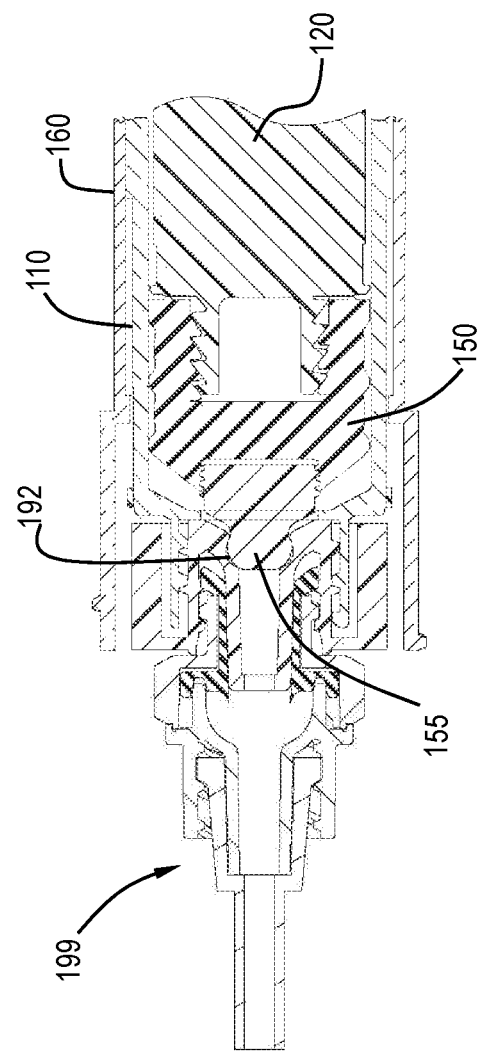
FIG. 26 shows an expanded cross-sectional view of the flush syringe assembly connected to the VAD after flushing with the stopper tip engaged with the cap in accordance with one or more embodiments of the invention.
Figure 27:
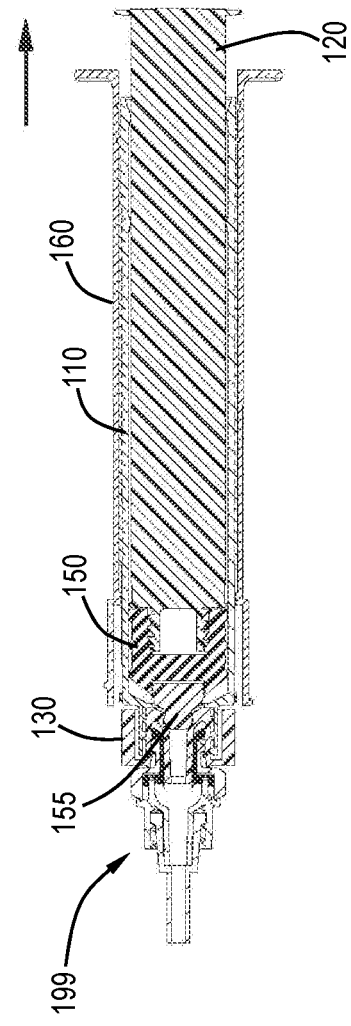
FIG. 27 shows a cross-sectional view of the flush syringe assembly connected to the VAD after flushing during the initial withdrawal stage with the cap exposed in accordance with one or more embodiments of the invention.
Figure 28:
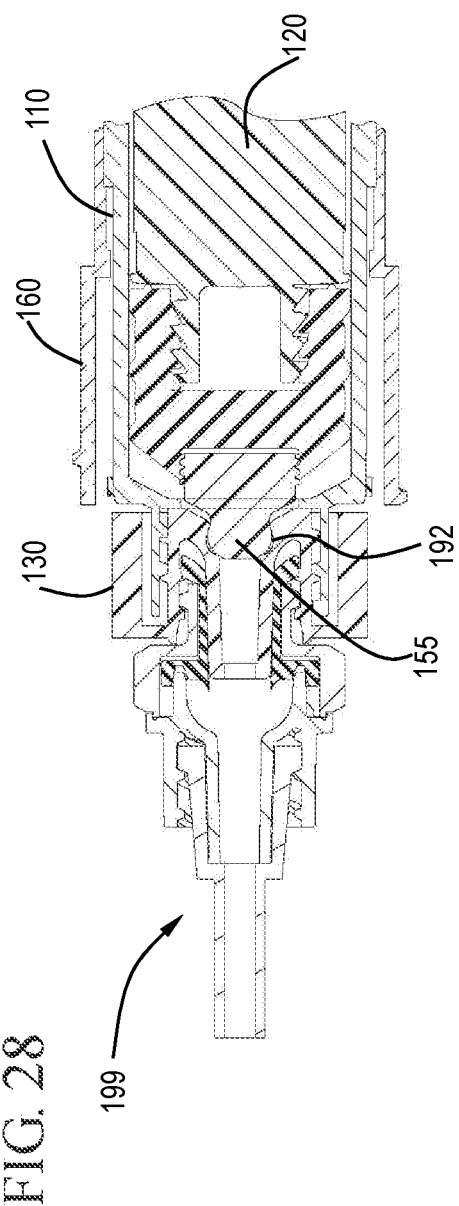
FIG. 28 shows an expanded cross-sectional view of the flush syringe assembly connected to the VAD after flushing with the cap exposed from under the sleeve in accordance with one or more embodiments of the invention.
Figure 29:
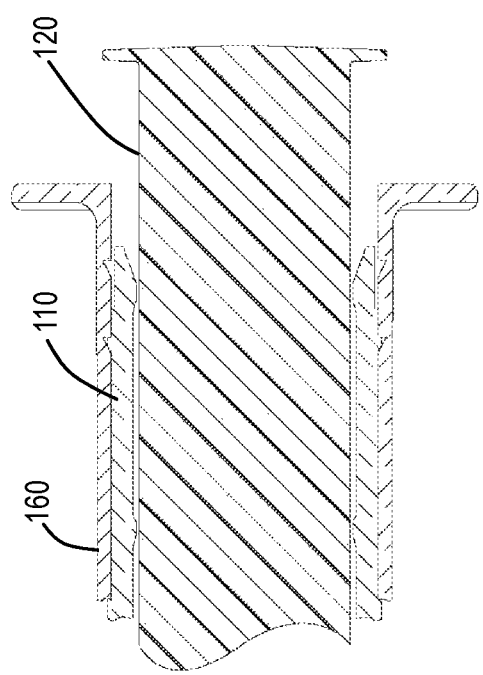
FIG. 29 shows an expanded cross-sectional view of the plunger rod, sleeve and barrel during removal in accordance with one or more embodiments of the invention.

FIGS. 25 and 26 show the plunger rod 120 and stopper 150 in the distal most position. Here, the distal end of the detachable stopper tip 155 has been forced into the undercut region 192 of the cap 130. FIGS. 27 and 28 show the sleeve 160 after proximal movement to expose the cap from the distal end of the sleeve. FIG. 29 shows the proximal end of the sleeve 160, barrel 110 and plunger rod 120 after the proximal movement to expose the cap 130.

Figure 30:
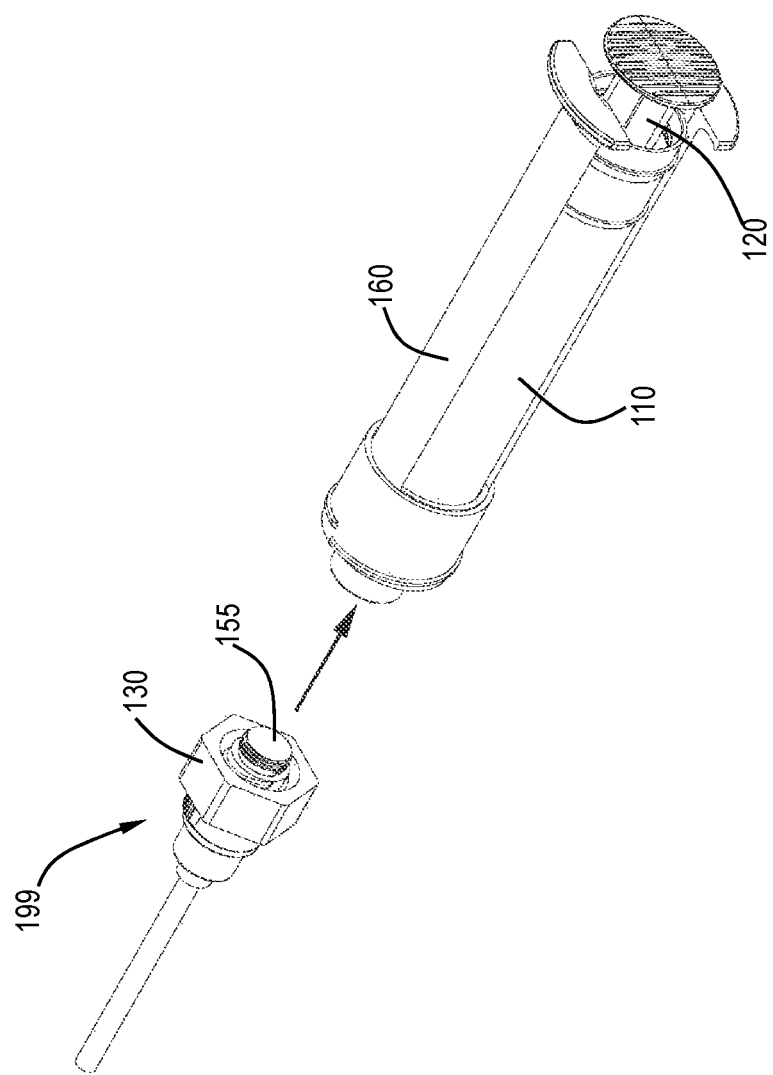
FIG. 30 shows a perspective view of the flush syringe assembly with the sleeve retracted being removed from the VAD leaving the cap and stopper tip in the VAD in accordance with one or more embodiments of the invention.
Figure 31:
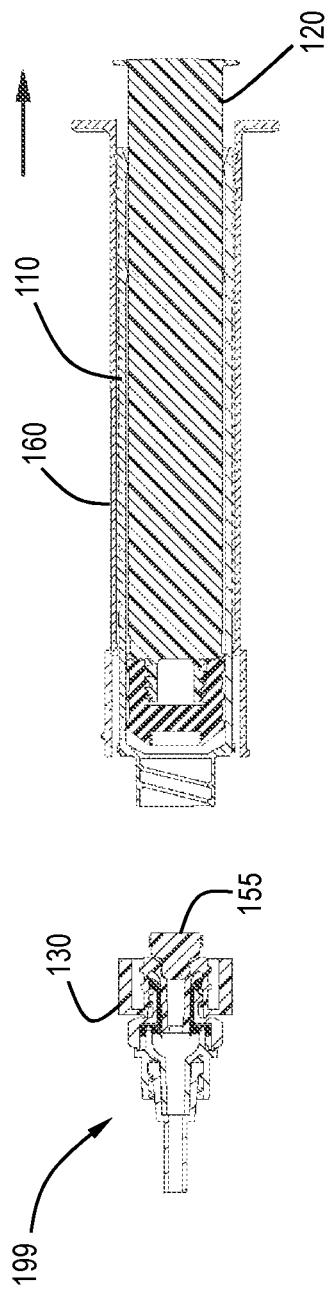
FIG. 31 shows a cross-sectional view of the flush syringe assembly and VAD after disconnection in accordance with one or more embodiments of the invention.
Figure 32:
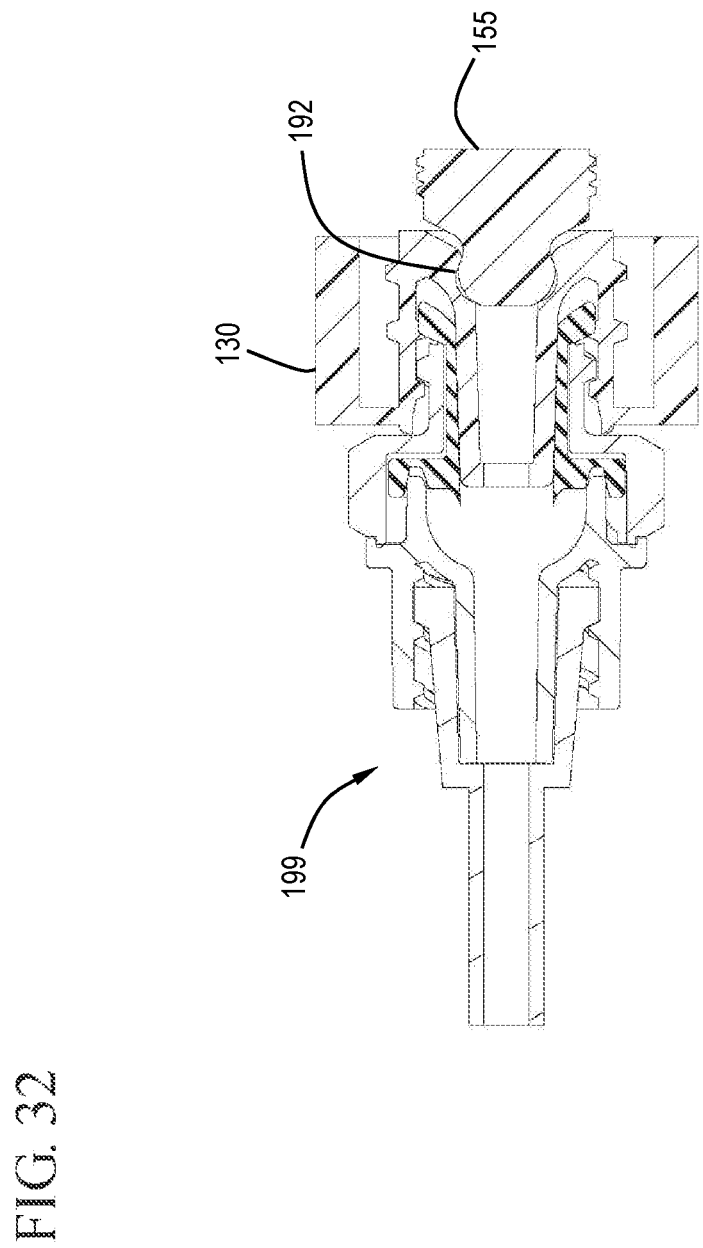
FIG. 32 shows an expanded cross-sectional view of the VAD with the cap and stopper tip embedded in the cap in accordance with one or more embodiments of the invention.

After the flush syringe is used, and the detachable stopper tip 155 has been forced into the undercut region 192 of the cap 130, the 130 and stopper tip 155 can be released from the distal end of the barrel 110 and left attached to the vascular access device 199, as shown in FIGS. 30 to 32. This is effective to cap off the vascular access device 199 to prevent contamination and minimize the need for future cleaning. Capping the VAD 199 also helps prevent blood refluxing through the VAD 199.

Additional embodiments of the invention are directed to methods of flushing a VAD. A flush syringe assembly, as described herein, is provided along with instructions regarding the proper operation of the flush syringe assembly. The flush syringe assembly is then used according the provided instructions.

Further embodiments of the invention are directed to methods of flushing a VAD comprising providing or receiving the flush syringe assembly described herein. One hand is used to remove the protective cover 185 from the distal end of the flush syringe assembly thereby exposing a disinfectant carrier 175 carrying a disinfectant. One hand is used to apply the disinfectant to the VAD connector. The same hand is used to eject the disinfecting system 170 from the distal end of the syringe assembly. The flush syringe assembly is coupled to the VAD. One hand is used to hold the flush syringe assembly and depress the plunger to flush the VAD with a flush solution that is contained within the syringe barrel (either prefilled or not prefilled). Using the same hand, the plunger rod is continued to be depressed after the barrel is empty to embed the stopper tip into the VAD and retract the sleeve to expose the cap 130. The cap including the embedded stopper tip is separated from the flush syringe assembly. In some embodiments, the cap with the embedded stopper tip can be removed from the VAD and the process can be repeated with another flush syringe assembly.

What is claimed is:

1. A method of preventing contamination of a vascular access device (VAD) while being worn by a patient comprising:
   providing a flush syringe assembly comprising a plunger rod, a disinfectant carrier comprising a disinfectant, and a cap;
   contacting the disinfectant carrier to the VAD;
   removing the disinfectant carrier from the flush syringe assembly;
   coupling the flush syringe assembly to the VAD;
   depressing the plunger rod of the flush syringe assembly to embed a stopper tip into the VAD to protect the VAD from contact with bacteria or other contaminants.

2. The method of claim 1 further comprising:
   (a) providing the flush syringe assembly further comprising
      a barrel,
      a sleeve external to the barrel having a distal end and a proximal end, and an inside surface and an outside surface, wherein the sleeve retracts from distal to proximal positions in relationship to a distal movement of the barrel,
      the disinfectant contained in a hub, the hub connected to the distal end of the sleeve, the disinfectant carrier comprising a protective cover on a distal end of the flush syringe assembly, and
      the cap comprising a proximal end for releasably attaching the cap to a distal end of the barrel and a distal end for releasably attaching the cap to the VAD;
   (b) using one hand to remove the protective cover from the distal end of the flush syringe assembly thereby exposing the disinfectant contained in the hub;
   (c) using one hand to apply the disinfectant to the VAD;
   (d) using the same hand as in (c) to perform the step of removing the disinfectant carrier from the flush syringe assembly upon proximal motion of the sleeve;
   (e) wherein the step of coupling the flush syringe assembly to the VAD includes coupling the distal end of the cap of the flush syringe assembly to the VAD;

(f) using one hand to hold the flush syringe assembly and depress a plunger rod disposed within the barrel to flush the VAD with a flush solution that is contained in a chamber of the barrel;

(g) using the same hand to perform the step of depressing the plunger rod of the flush syringe assembly to embed a stopper tip into the VAD and retract the sleeve to expose the cap.

3. The method of claim 2, wherein the barrel of the flush syringe assembly comprises a side wall having an inside surface defining a chamber for retaining fluid, an outside surface, an open proximal end, a distal end including a distal wall having a passageway therethrough in fluid communication with the chamber.

4. The method of claim 2, wherein the plunger rod is disposed within the barrel, the plunger rod comprising a distal end including a stopper slidably positioned in fluid-tight contact with an inside surface of the barrel for driving fluid out of the chamber by movement of the stopper relative to the barrel, wherein the stopper comprises a stopper body and a detachable stopper tip.

5. The method of claim 4, wherein the stopper tip has threads which engage with complementary threads on the stopper body.

6. The method of claim 4, wherein the stopper tip is secured to the stopper body using an interference fit.

7. The method of claim 4, wherein the stopper body is made of material selected from the list consisting of thermoplastic elastomers, natural rubber, synthetic rubber, thermoplastic materials and combinations thereof.

8. The method of claim 4, wherein the stopper tip is made of material selected from the list consisting of thermoplastic elastomers, natural rubber, synthetic rubber, thermoplastic materials and combinations thereof.

9. The method of claim 2, wherein the cap comprises an outer wall surrounding a threaded connection, wherein the cap comprising a passageway for fluid communication therethrough, wherein the passageway is undercut to receive and retain the stopper tip when the plunger rod is fully depressed, the cap further comprises a distal end for releasably attaching the cap to a vascular access device (VAD) and a proximal end for releasably attaching the cap to the barrel.

10. The method of claim 9, wherein the undercut of the passageway of the cap creates a tight interference fit sufficient for retaining the stopper tip within the cap upon movement of the plunger rod away from the cap after emptying the fluid from the syringe.

11. The method of claim 9, wherein coupling the flush syringe assembly to the VAD comprises engaging complementary threads on the cap with the VAD.

12. The method of claim 9, wherein coupling the flush syringe assembly to the VAD comprises engaging the cap to the VAD with an interference fit.

13. The method of claim 2, wherein the sleeve further comprises one or more cutouts to provide visibility to the flush solution of the barrel.

14. The method of claim 2, wherein an outside surface of the barrel further comprises two annular positioning ridges, a distal annular positioning ridge and a proximal annular positioning ridge.

15. The method of claim 14, wherein the inside surface of the sleeve further comprises at least one annular positioning groove for controlling the position of the sleeve relative to the barrel by engaging with the annular positioning ridges on the outside surface of the barrel.

16. The method of claim 15, wherein the outside surface of the barrel comprises one or more ridges that extend along a length of the barrel and engage with a corresponding groove on the inside surface of the sleeve.

17. The method of claim 2, wherein the disinfectant is made of material selected from the list consisting of alcohol, an antiseptic gel and combinations thereof.

18. The method of claim 9, wherein the passageway of the cap is coated with an antimicrobial agent.

\* \* \* \* \*